United States Patent
Creasey

(10) Patent No.: US 7,674,769 B2
(45) Date of Patent: Mar. 9, 2010

(54) TREATMENT OF SEVERE PNEUMONIA BY ADMINISTRATION OF TISSUE FACTOR PATHWAY INHIBITOR (TFPI)

(75) Inventor: Abla Creasey, Piedmont, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 1254 days.

(21) Appl. No.: 10/270,478

(22) Filed: Oct. 15, 2002

(65) Prior Publication Data

US 2003/0139339 A1 Jul. 24, 2003

Related U.S. Application Data

(60) Provisional application No. 60/328,806, filed on Oct. 15, 2001.

(51) Int. Cl.
*A61K 38/57* (2006.01)
*C07K 14/81* (2006.01)

(52) U.S. Cl. .................. 514/12; 930/250; 530/380; 530/350; 530/395

(58) Field of Classification Search .................. None
See application file for complete search history.

(56) References Cited

U.S. PATENT DOCUMENTS

| | | |
|---|---|---|
| 4,179,337 A | 12/1979 | Davis et al. |
| 4,399,216 A | 8/1983 | Axel et al. |
| 4,495,285 A | 1/1985 | Shimizu et al. |
| 4,511,502 A | 4/1985 | Builder et al. |
| 4,530,787 A | 7/1985 | Shaked et al. |
| 4,569,790 A | 2/1986 | Koths et al. |
| 4,572,798 A | 2/1986 | Koths et al. |
| 4,599,176 A | 7/1986 | Wittenberger |
| 4,603,106 A | 7/1986 | Cerami et al. |
| 4,609,546 A | 9/1986 | Hiratani |
| 4,620,948 A | 11/1986 | Builder et al. |
| 4,683,195 A | 7/1987 | Mullis et al. |
| 4,683,202 A | 7/1987 | Mullis |
| 4,711,845 A | 12/1987 | Gelfand et al. |
| 4,748,234 A | 5/1988 | Dorin et al. |
| 4,766,106 A | 8/1988 | Katre et al. |
| 4,847,201 A | 7/1989 | Kawasaki et al. |
| 4,929,700 A | 5/1990 | Halenbeck et al. |
| 4,966,852 A | 10/1990 | Wun et al. |
| 5,106,833 A | 4/1992 | Broze et al. |
| 5,110,730 A | 5/1992 | Edgington et al. |
| 5,212,091 A | 5/1993 | Diaz-Collier et al. |
| 5,219,994 A | 6/1993 | Buonassisi et al. |
| 5,223,427 A | 6/1993 | Edgington et al. |
| 5,276,015 A | 1/1994 | Khouri et al. |
| 5,563,123 A | 10/1996 | Innis et al. |
| 5,736,364 A | 4/1998 | Kelley et al. |
| 5,859,005 A | 1/1999 | Mohan et al. |
| 5,874,407 A | 2/1999 | Kelley et al. |
| 5,885,781 A | 3/1999 | Johnson et al. |
| 5,888,968 A | 3/1999 | Chen et al. |
| 5,902,582 A | 5/1999 | Hung |
| 5,914,316 A | 6/1999 | Brown et al. |
| 5,977,057 A | 11/1999 | Van't Veer et al. |
| 5,981,471 A | 11/1999 | Papathanassin et al. |
| RE36,476 E | 12/1999 | Khouri et al. |
| 6,008,199 A | 12/1999 | Grinnell et al. |
| 6,060,449 A | 5/2000 | Hamuro et al. |
| 6,063,764 A | 5/2000 | Creasey et al. |
| 6,156,734 A | 12/2000 | Grinnell et al. |
| 6,159,468 A | 12/2000 | Carlson et al. |
| 6,180,607 B1 | 1/2001 | Davies et al. |
| 6,238,878 B1 | 5/2001 | Jakobsen et al. |
| 6,242,414 B1 | 6/2001 | Johnson et al. |
| 6,268,344 B1 | 7/2001 | Grinnell et al. |
| 6,270,764 B1 | 8/2001 | Fisher et al. |
| 6,294,648 B1 | 9/2001 | Delaria et al. |
| 6,323,326 B1 | 11/2001 | Dorin et al. |
| 6,344,197 B2 | 2/2002 | Fisher et al. |
| 6,395,270 B1 | 5/2002 | Carlson et al. |
| 6,444,434 B1 | 9/2002 | Jakobsen et al. |
| 6,489,296 B1 | 12/2002 | Grinnell et al. |
| 6,525,102 B1 | 2/2003 | Chen et al. |
| 6,660,852 B1 * | 12/2003 | Keshi et al. ............... 536/24.32 |
| 6,824,997 B1 * | 11/2004 | Moore et al. ............... 435/7.34 |
| 2001/0006806 A1 | 7/2001 | Fisher et al. |

(Continued)

FOREIGN PATENT DOCUMENTS

| | | |
|---|---|---|
| EP | 268110 B1 | 5/1988 |
| EP | 270799 B1 | 6/1988 |
| EP | 318451 B1 | 5/1989 |
| EP | 473564 A1 | 3/1992 |
| EP | 473564 B1 | 3/1992 |
| JP | 08143471 A * | 6/1996 |
| WO | WO - 85/04899 | 11/1985 |
| WO | WO - 90/08158 | 7/1990 |
| WO | WO - 91/02753 | 3/1991 |
| WO | WO - 91/19514 | 12/1991 |

(Continued)

OTHER PUBLICATIONS

Khouri et al. A phase II trial of intraluminal irrigation with recombinant human tissue factor pathway inhibitor to prevent thrombosis in free flap surgery. Plast Reconstr Surg. Feb. 2001;107(2):408-15.*

(Continued)

*Primary Examiner*—David S Romeo
(74) *Attorney, Agent, or Firm*—Banner & Witcoff, Ltd.

(57) ABSTRACT

Methods for prophylactically or therapeutically treating severe pneumonia involve administration of tissue factor pathway inhibitor (TFPI) or a TFPI analog to patients suffering from or at risk of developing this condition. The methods involve the use of continuous intravenous infusion of TFPI or a TFPI analog, preferably at low doses to avoid adverse side effects.

53 Claims, No Drawings

U.S. PATENT DOCUMENTS

| | | |
|---|---|---|
| 2001/0018204 A1 | 8/2001 | Papathanassin et al. |
| 2001/0028880 A1 | 10/2001 | Fisher et al. |
| 2001/0051154 A1 | 12/2001 | Roemisch et al. |
| 2002/0006896 A1 | 1/2002 | Johnson et al. |
| 2002/0006897 A1 | 1/2002 | Johnson et al. |
| 2002/0032150 A1 | 3/2002 | Johnson et al. |
| 2002/0137884 A1 | 9/2002 | Dorin et al. |
| 2002/0177560 A1 | 11/2002 | Greenfield et al. |
| 2002/0177563 A1 | 11/2002 | Griffin et al. |
| 2002/0197667 A1 | 12/2002 | Inis et al. |
| 2002/0198138 A1 | 12/2002 | Macias |
| 2003/0007966 A1 | 1/2003 | Hoffmann et al. |
| 2003/0022354 A1 | 1/2003 | Gerlitz et al. |
| 2003/0073638 A1 | 4/2003 | Kjalke |

FOREIGN PATENT DOCUMENTS

| | | |
|---|---|---|
| WO | WO - 92/06711 | 4/1992 |
| WO | WO - 92/07584 | 5/1992 |
| WO | WO 93/24143 | 12/1993 |
| WO | WO - 93/25230 | 12/1993 |
| WO | WO 93/25230 | 12/1993 |
| WO | 96/40784 A2 | 12/1996 |
| WO | WO 99/00418 | 1/1999 |
| WO | WO 00/77254 | * 12/2000 |
| WO | WO 01/49315 | 7/2001 |
| WO | WO 01/60837 | 8/2001 |
| WO | WO 03/032904 | 4/2003 |

OTHER PUBLICATIONS

Poller et al. Fixed minidose warfarin: a new approach to prophylaxis against venous thrombosis after major surgery. British Medical Journal (Clinical Research Edition). Nov. 21, 1987, vol. 295 No. 6609, pp. 1309-1312.*

Oltrona et al. Inhibition of tissue factor-mediated coagulation markedly attenuates stenosis after balloon-induced arterial injury in minipigs. Circulation. Jul. 15, 1997, vol. 96 No. 2, pp. 646-652.*

Waterer et al. Septic shock and respiratory failure in community-acquired pneumonia have different TNF polymorphism associations. Am J Respir Crit Care Med. Jun. 2001;163(7):1599-604.*

Ruiz et al. Severe community-acquired pneumonia. Risk factors and follow-up epidemiology. Am J Respir Crit Care Med. Sep. 1999;160(3):923-9.* heparin . ( 2008). In Encyclopædia Britannica. Retrieved Jul. 4, 2008, from Encyclopædia Britannica Online: http://www.search.eb.com/eb/article-9040075.*

Feldman et al., "Anti-TNF alpha therapy is useful in rheumatoid arthritis and Crohn's disease: Analysis of the mechanism of action predicts utility in other diseases.", Transplantation Proc., Dec. 1998, vol. 30, No. 8, pp. 4126-4127.

Bajaj et al., "Tissue factor pathway inhibitor expression by human pleural mesothelial and mesothelioma cells," Eur Respir J, 2000; vol. 15, 1069-1078.

Dehoux et al.. Compartmentalized Cytokine Production within the Human Lung in Unilateral Pneumonia, Aj J Respir Crit Care Med., vol. 150, pp. 710-716, 1994.

Boutten et al., "Compartmentalized IL-8 and Elastase Release within the Human Lung in Unilateral Pneumonia", Am J. Respir Crit Care Med., vol. 153, pp. 336-342, 1996.

De Moerloose et al., "Procoagulant activity in bronchoalveolar fluids: No relationship with tissue factor pathway inhibitor activity", Thrombosis Research, vol. 65, pp. 507-518, 1992.

Günther et al., "Alveolar Fibrin Formation Caused by Enhanced Procoagulant and Depressed Fibrinolytic Capacities in Severe Pneumonia," Am J Respir Crit Care Med, vol. 161, pp. 454-462, 2000.

Schaaf at al., "Neutrophil Inflammation and Activation in Bronchiectasis: Comparison with Pneumonia and Idiopathic Pulmonary Fibrosis", Respiration, vol. 67, pp. 52-59, 2000.

Van't veer et al., "Inhibitory Mechanism of the Protein C Pathway on Tissue Factor-induced Thrombin Generation", The Journal of Biological Chemistry, vol. 272, No. 12, pp. 2983-7994, Mar. 21, 1997.

Abraham, "Tissue Factor Inhibition and Clinical Trial Results of Tissue Factor Pathway Inhibitor in Sepsis", *Critical Care Medicine*, 28(9), pp. S31-S33 (2000).

Abraham, "Coagulation Abnormalities in Acute Lung Injury and Sepsis", *Am. J. Respir. Cell Mol. Biol.* 22(4), pp. 401-404 (Apr. 2000).

Abraham et al., "Efficacy and Safety of Tifacogin (Recombinant Tissue Factor Pathway Inhibitor) in Severe Sepsis; A Randomized Controlled Trial", JAMA, Jul. 9, 2003, pp. 238-247, vol. 290, No. 2, American Medical Association.

Alban et al., "Plasma Levels of Total and Free Tissue Factor Pathway Inhibitor (TFPI) as Individual Pharmacological Parameters of Various Heparins", *Thromb. Haemost.* 85(5):824-9 (May 2001).

Ameri et al., "Expression of Tissue Factor Pathway Inhibitor by Cultured Endothelial Cells in Response to Inflammatory Mediators", *Blood*, 79:3219-3226 (1992).

Angus et al., "Unraveling Severe Sepsis; Why did Optimist Fail and What's Next?," JAMA, Jul. 9, 2003, pp. 256-258, vol. 290, No. 2, American Medical Association.

Badimon, "Potential therapeutic indications for Tissue Factor Inhibition," The IBC International Symposium on Advances in Anticoagulant, Anti-thrombotic and Thrombolitic Drugs (Sep. 11, 1998).

Bailey et al., "Methylmercury as a Reversible Denaturing Agent for Agarose Gel Electrophoresis", *Anal. Bioch.*, 70:75-85 (1976).

Bajaj et al., "Cultured Normal Human Hepatocytes do not Synthesize Lipoprotein-Associated Coagulation Inhibitor: Evidence that Endothelium is the Principal Site of its Synthesis", *PNAS* (USA), 87:8869-8873 (1990).

Bajaj et al., Inhibitor of the Factor VIIa-Tissue Factor Complex is Reduced in Patients with Disseminated Intravascular Coagulation but not in Patients with Severe Hepatocellular Disease, *J. Clin. Invest.*, 79:1874-1878 (1987).

Bevilacqua et al., "Recombinant Tumor Necrosis Factor Induces Procoagulant Activity in Cultured Human Vascular Endothelium: Characterization and Comparison with the Actions of Interleukin 1", *PNAS* (USA), 83:4533-4537 (1986).

Bolivar et al., "Construction and Characterization of New Cloning Vehicles", *Gene*, 2:95-113 (1977).

Bone et al., "Definitions for Sepsis and Organ Failure and Guidelines for the Use of Innovative Therapies in Sepsis", *Chest*, 101:1644-1655 (1992).

Boosman et al., "Nontraditional Methods Used to Determine the Disulfide Bonds of Human Tissue Factor Pathway Inhibitor from *E. coli*", 11th International Conference on Methods in Protein Structure Analysis (Sep. 5, 1998).

Braeckman et al., "Population PK/PD Modeling and Computer Assisted Trial Design (CATD) in Clinical Drug Development—A Case Example," 8th Annual Workshop on Advanced Methods of Pharmacokinetic and Pharmacodynamic Systems Analysis at Marina del Rey, CA (Jun. 25-26, 1999).

Broach, "Construction of High Copy Yeast Vectors Using 2-μm Circle Sequences", *Methods in Enzymology*, 101:307-325 (1983).

Broach et al., "Transformation in Yeast: Development of a Hybrid Cloning Vector and Isolation of the CANI Gene", *Gene*, 8:121-133 (1979).

Broze et al., "Regulation of Coagulation by a Multivalent Kunitz-Type Inhibitor", *Biochemistry*, 29:7539-7546 (1990).

Broze et al., "The Lipoprotein-Associated Coagulation Inhibitor that Inhibits the Factor VII-Tissue Factor Complex Also Inhibits Factor Xa: Insight Into Its Possible Mechanism of Action", *Blood*, 71:335-343 (1988).

Broze of al., "Isolation of the Tissue Factor Inhibitor Produced by HepG2 Hepatoma Cells", *PNAS* (USA),84:1886-1890 (1987).

Brozna, "Cellular Regulation of Tissue Factor", *Blood Coagulation Fibrinolysis*, 1:415-426 (1990).

Callander et al., "Mechanisms of Binding of Recombinant Extrinsic Pathway Inhibitor (rEPI) to Cultured Cell Surfaces", *The Journal of Biological Chemistry*, 267:876-882 (1992).

Camerota et al., "Delayed Treatment with Recombinant Human Tissue Factor Pathway Inhibitor Improves Survival in Rabbits with Gram-Negative Peritonitis", *J. Infect. Dis.*;177(3):668-76 (Mar. 1998).

Clarke et al., "Selection Procedure for Isolation of Centromere DNAs from *Saccharomyces cerevisiae*", *Meth. Enzymol.*, 101:300-325 (1983).

Clewell et al., "Nature of Col. $E_1$ Plasmid Replication in *Escherichia coli* in the Presence of Chloramphenicol", *J. Bacteriol.*, 110:667-676 (1972).

Clewell et al., "Supercoiled Circular DNA-Protein Complex in *Escherichia coli*: Purification and Induced Conversion to an Open Circular DNA Form", *PNAS* (USA ), 62:1159-1166 (1969).

Cohen et al., "Nonchromosomal Antibiotic Resistance in Bacteria: Genetic Transformation of *Escherichia coli* by R-Factor DNA", *PNAS* (USA), 69:2110-2114 (1972).

Colucci et al., "Cultured Human Endothelial Cells Generate Tissue Factor in Response to Endotoxin", *J. Clin. Invest.*, 71:1893-1896 (1983).

Corrigan, "Heparin Therapy in Bacterial Septicemia", J. Pediatrics. 91:695-700 (1977).

Corrigan et al., "Heparin Therapy in Septicemia with Disseminated Intravascular Coagulation. Effect on Mortality and on Correction of Hemostatic Defects". N. *Engl. J. Med.*, 283:778-782 (1970).

Creasey, "New Potential Therapeutic Modalities: Tissue Factor Pathway Inhibitor," *Sepsis*, 3: 173-182 (1999).

Creasey et al., "Tissue Factor Pathway Inhibitor Activity in Severe Sepsis", *Crit. Care Med.*, 29(7 Suppl.): S126-S129 (2001).

Creasey, "TFPI Biology and Pharmacology", IBC $8^{th}$ Annual Conference on Sepsis, Endotoxemia & Related Disorders (Jan. 20, 1999).

Creasey, "Investigation of Tifacogin (Recombinant Tissue Factor Pathway Inhibitor) in Severe Sepsis", ICAAC Meeting (Sep. 26, 1999).

Creasey, "Investigation of Tifacogin (rTFPI) for Severe Sepsis", Crit. Care Med. (Oct. 28, 1999).

Creasey, "Investigation of Tifacogin (rTFPI) for Severe Sepsis", $5^{th}$ World Congress on Trauma, Shock, Inflammation and Sepsis (Nov. 30, 1999).

Creasey et al., "Tissue Factor Pathway Inhibitor Reduces Mortality from *Escherichia coli* Septic Shock", *J. Clin. Invest.*, 91 (Jun.):2850-2860 (1993).

Creasey et al., "Endotoxin and Cytokine Profile in Plasma of Baboons Challenged With Lethal and Sublethal *Escherichia coli*", *Circ. Shock*, 33:84-91 (1991).

Cross et al., "Choice of Bacteria in Animal Models of Sepsis", *Infect. Immun.*, 61:2741-2747 (1993).

Day et al., "Recombinant Lipoprotein-Associated Coagulation Inhibitor Inhibits Tissue Thromboplastin-Induced Intravascular Coagulation in the Rabbit", *Blood*, 76, No. 8 (Oct. 15):1538-1545 (1990).

deJonge et al., "Tissue Factor Pathway Inhibitor Dose-Dependently Inhibits Coagulation Activation without Influencing the Fibrinolytic and Cytokine Response During Human Endotoxemia", *Blood* 95(4):1124-1129 (Feb. 15, 2000).

deJonge et al., "Tissue Factor Pathway Inhibitor Does Not Influence Inflammatory Pathways During Human Endotoxemia", *J. Infect. Dis.* 183(12): 1815-1818 (Jun. 2001).

Depicker et al., "Nopaline Synthase: Transcript Mapping and DNA Sequence", J. Mol. *Appl. Gen.* 1:561-573 (1982).

Dhainaut et al., "Combined Procoagulant and Innate Immune Responses to Infection: Toward More Potent Drugs in Septic Patients", *Crit. Care Med.* 29(1):205-207 (Jan. 2001).

Fiers et al., "Complete Nucleotide Sequence of SV40 DNA", *Nature*, 273:113-120 (1978).

Fink et al., "Laboratory Models of Sepsis and Septic Shock", *Journal of Surgical Research*, 49:186-196 (1990).

Fischer et al., "Interleukin-I Receptor Blockade Improves Survival and Hemodynamic Performance in *Escherichia coli* Septic Shock, but Fails to Alter Host Responses to Sublethal Endotoxemia", J. *Clin. Invest.*, 89:1551-1557 (1992).

Girard et al., "Truncated Tissue Factor Pathway Inhibitor Protects Baboons from Lethal Doses of *E. coli*", *Blood, Coagulation & Fibrinolysis* (2000).

Girard et al., "Identification of the 1.4 KB and 4.0 KB Messages for the Lipoprotein Associated Coagulation Inhibitor and Expression of the Encoded Protein", *Thrombosis Research*, 55:37-50 (1989).

Girard et al., "Functional Significance of the Kunitz-type Inhibitory Domains of Lipoprotein-Associated Coagulation Inhibitor", *Nature*, 338:518-520 (1989).

Goeddel et al., "Synthesis of human fibroblast interferon by *E. coli*", *Nucl. Acids Res.*, 8:4057-4074 (1980).

Graham et al., "A New Technique for the Assay of Infectivity of Human Adenovirus 5 DNA", *Virology*, 52:456-467 (1973).

Hall et al., "The Association of TFPI with Artificial Surfaces", $6^{th}$ World Biomaterials Congress.

Hamamoto at al., "Inhibitory Properties of Full-length and Truncated Recombinant Tissue Factor Pathway Inhibitor (TFPI)", *J. Biol. Chem.*, 268:8704-8710 (1993).

Haskel et al., "Prevention of Arterial Reocclusion After Thrombolysis With Recombinant Lipoprotein-Associated Coagulation Inhibitor", *Circulation*, 84:821-827 (1991).

Hess et al., "Cooperation of Glycolytic Enzymes", J. *Adv. Enzyme Reg.*, 7:149-167 (1968).

Hinshaw, et al., "Survival of Primates in $LD_{100}$ Septic Shock Following Steroid/Antibiotic Therapy", *J. Surg. Res.*, 28:151-170 (1989).

Hinshaw et al., "Detection of the 'Hyperdynamic State' Sepsis in the Baboon during Lethal *E. coli* Infusion", *J. Trauma*, 23:361-365 (1983).

Hinshaw et al., "Survival of Primates in $LD_{100}$ Septic Shock Following Therapy with Antibody to Tumor Necrosis Factor (TNFα)", *Circulatory Shock*, 30:279-292 (1990).

Hitzeman et al., "Isolation and Characterization of the Yeast 3-Phosphoglycerokinase Gene (PGK) by an Immunological Screening Technique", *J. Biol. Chem.*, 255:12073-12080 (1980).

Holland et al., "The Primary Structures of Two Yeast Enolase Genes", *J. Biol. Chem.*, 256:1385-1395 (1981).

Holland et al., "Isolation and Identification of Yeast Messenger Ribonucleic Acids Coding for Enolase, Glyceraldehyde-3-phosphate Dehydrogenase, and Phosphogiycerate Kinase", *Biochemistry*, 17:4900-4907 (1978).

Holst et al., "Antithrombotic Properties of a Truncated Recombinant Tissue Factor Pathway Inhibitor in an Experimental Venous Thrombosis Model", *Haemostasis*, 23(Suppl 1):112-117 (1993).

Hsiao at al., "High-Frequency Transformation of Yeast by Plasmids Containing the Cloned Yeast ARG4 Gene", *PNAS* (USA) 76:3829-3833 (1979).

Kaus, "Pharmacokinetics and Pharmacodynamics of Recombinant Tissue Factor Pathway Inhibitor (r-TFPI): Effect of IV and SC Heparin Administration," AAPS Annual Meeting (Oct. 29, 1999).

Kemme et al., "The Influence of Reduced Liver Blood Flow (LBF) on the Pharmacokinetics (PK) of Recombinant Tissue Factor Pathway Inhibitor (rTFPI)", 1999 American Society for Clinical Pharmacology Therapeutics Meeting.

Knauf et al., "Relationship of Effective Molecular Size to Systemic Clearance in Rats of Recombinant Interleukin-2 Chemically Modified with Water-Soluble Polymers", *J. Biol. Chem.*, 263:15064-5070 (1988).

Kristensen et al., "Effect of Tissue Factor Pathway Inhibitor (TFPI) in the Heptest® Assay and in an Amidolytic Anti Factor Xa Assay for LMW Heparin", *Thrombosis flaemost.*, CF.K. Schattauer Verlagsgesellschaft mbH (Stuttgart) 68:310-314 (1992).

Kunkel et al., "Rapid and Efficient Site-Specific Mutagenesis without Phenotypic Selection", *Proc. Nat. Acad. Sci. USA*, 82:488-492 (1985).

Lasch et al., "Heparin Therapy of Diffuse Intravascular Coagulation (DIC)", *Thrombos. Diathes.. Haemorrh.* (*Stuttg.*), 33:105-106 (1974).

Lee et al., "Coagulation Inhibitors in Sepsis and Disseminated Intravascular Coagulation", *Intensive Care Med.* 26(11):1701-6 (Nov. 2000).

Leighton, "Tissue Factor Pathway Inhibitor Biology and Pharmacology", ISTH (Aug. 14, 1999).

Levi et al., "Novel Approaches to the Management of Disseminated Intravascular Coagulation", *Crit. Care Med.* 28(9 Suppl):S20-4 (Sep. 2000).

Lindhout et al., "Activation of Factor X and Its Regulation by Tissue Factor Pathway Inhibitor in Small-Diameter Capillaries Lined With Human Endothelial Cells", *Blood*, 79:2909-2916 (1992).

Lyberg et al., "Cellular Cooperation in Endothelial Cell Thromboplastin Synthesis", *British* Journal of *Haemotology*, 53:85-95 (1983).

Maniatas et al., *Molecular Cloning—A Laboratory Manual*, Cold Spring Harbor Press, p. 202-203 (1982).

Martin et al., "Prospective National Study of Gram-Negative Bacterial (GNB) Sepsis—Natural History in the 1980s", Abstract No. 317, 29th ICAAC Meeting, Houston (1989).

Matteucci et al., "Synthesis of Deoxyoligonucleotides on a Polymer Support", *J. Am. Chem. Soc.*, 103:3185-3191 (1981).

Matyal et al., "Extremely Low Doses of TFPI Decrease Mortality in a Rabbit Model of Septic Shock", *Intensive Care Med.*, 27(8):1274-1280 (Aug. 2001).

Maxam et al., "Sequencing End-Labeled DNA with Base-Specific Chemical Cleavages", *Meth. Enzymol.*, 65:499-560 (1980).

Messing et al., "A System for Shotgun DNA Sequencing", *Nud Acids Res.*, 9:309-321 (1981).

MMWR, *Septicemia*, 39(2):31-34 (1987).

MMWR, *Hospitalizations*, 39(43):777-785 (1987).

Müller-Berghaus, "Pathophysiologic and Biochemical Events in Disseminated Intravascular Coagulation: Dysregulation of Procoagulant and Anticoagulant Pathways", *Seminars in Thrombosis and Haemostasis*, 15:58-87 (1989).

Nawroth et al., "Interleukin 1 Induces Endothelial Cell Procoagulant While Suppressing Cell-Surface Anticoagulant Activity", *PNAS* (USA), 83:3460-3464 (1986).

Nemerson, "Tissue Factor and Hemostasis", *Blood*, 71:1-8 (1988).

Novotny et al., "Purification and Properties of Heparin-Releasable Lipoprotein-Associated Coagulation Inhibitor", *Blood*, 78:394-400 (1991).

Novotny et al., "Purification and Characterization of the Lipoprotein-Associated Coagulation Inhibitor from Human Plasma", *J. Biol. Chem.*, 264:18832-18837 (1989).

Nordfang et al., "Inhibition of Extrinsic Pathway Inhibitor Shortens the Coagulation Time of Normal Plasma and of Hemophilia Plasma", *Thrombosis and Haemostasis*, F.K. Schattauer Verlagsgesellschaft mbH (Stuttgart) 55:464-467 (1991).

Nordfang at el., "The C-Terminus of Tissue Factor Pathway Inhibitor Is Essential to Its Anticoagulant Activity", *Biochemistry*, 30:10371-10376 (1991).

Obukowicz, et al., "Secretion of Active Kringle-2-Serine Protease in *Escherichia coli*", *Biochemistry*, 29:9737-9745 (1990).

Olins et al., "A Novel Sequence Element Derived from Bacteriophage T7 mRNA Acts as an Enhancer of Translation of the IacZ Gene in *Escherichia coli*", Journal of *Biological Chemistry*, 264:16973-16976 (1989).

Opal et al., "The Activity of Tissue Factor Pathway Inhibitor (TFPI) in Experimental Models of Superantigen-Induced and Polymicrobial Sepsis", ICAAC, Apr. 27, 1999, Abstract Only.

Ostergaard et al., *Haemostasis*, 23:221-222 (1993).

Osterud et al., "Increased Tissue Thromboplastin Activity in Monocytes of Patients with Meningococcal Infection: Related to an Unfavourable Prognosis", *Thrombosis Haemost.*, 49:5-7 (1983).

Ott et al., "Reversible Regulation of Tissue Factor-Induced Coagulation by Phosphatidylinositol-Anchored Tissue Factor Pathway Inhibitor", *Arterioscler. Thromb. Vasc. Biol.* 20(3):874-82 (Mar. 2000).

Pedersen et al., "Recombinant Human Extrinsic Pathway Inhibitor", *J. Biol. Chem.*, 265:16786-16793 (1990).

Petersen et al., "Effect of Leukocyte Proteinases on Tissue Factor Pathway Inhibitor", *Thrombosis and Haemostasis, of* F.K. Schattauer Verlagsgesellschaft mbH (Stuttgart) 67:537-541 (1992).

Quezado et al., "Therapies Directed Against Endotoxin—Has the Time Come?", Western *J. of Med.*,158:424-425 (1993).

Rapaport, "Inhibition of Factor VIIa/Tissue Factor-Induced Blood Coagulation: With Particular Emphasis Upon a Factor Xa-Dependent Inhibitory mechanism", *Blood*, 73: 359-365 (1989).

Rapaport, "The Extrinsic Pathway Inhibitor: A Regulator of Tissue Factor-Dependent Blood Coagulation", *Thrombosis Haemost.*, 66:6-15 (1991).

Reinhart, "Overview of Tifacogin Clinical Development" Brussels, Scientific Conference (2001).

Rivers et al., "The Endotoxin-induced Coagulant Activity of Human Monocytes", Br J. *Haematol.*, 30:311-316 (1975).

Sandset et al., "Coagulation Iinhibitor Levels in Pneumonia and Stroke: Changes due to Consumption and Acute Phase Reaction" J. *Internal Med.*225:311-316 (1989).

Sandset et al., "Depletion of Extrinsic Pathway Inhibitor (EPI) Sensitizes Rabbits to Disseminated Intravascular Coagulation Induced with Tissue factor: Evidence Supporting a Physiologic Role for EPI as a Natural Anticoagulant", *PNAS* (USA ), 88:708-712 (1991).

Sandset et al., "Extrinsic Pathway Inhibitor in Postoperative/Post-traumatic Septicemia: Increased Levels in Fatal Cases", *Haemostasis*, 19:189-195 (1989) (Abstract).

Sandset et al., "Immunodepletion of Extrinsic Pathway Inhibitor Sensitizes Rabbits to Endotoxin-Induced Intravascular Coagulation and the Generalized Shwartzman Reaction", *Blood*, 78:1496-1502 (1991).

Sandset et al., "Heparin Induces Release of Extrinsic Coagulation Pathway Inhibitor (EPI)", *Thrombosis Res.*, 50:808-813 (1988).

Sanger et al., "DNA sequencing with chain-terminating inhibitors", *PNAS* (USA), 74:5463-5467 (1977).

Sehgal et al., "Heterogeneity of Poly(I).Poly(C)-Induced Human Fibroblast Interferon mRNA Species", *Nature*, 288:95-97 (1980).

Shaw et al., "A General Method for the Transfer of Cloned Genes to Plant Cells", *Gene*, 23:315-330 (1983).

Shimatake et al., "Purified λ Regulatory Protein cII Positively Activates Promoters for Lysogenic Development", *Nature*, 292:128-132 (1981).

Stephenson et al., "Tissue Factor Pathway Inhibitor Delays the Development of Intimal Hyperplasia in a Porcine Vein-Grafting Model", American College of Surgery, Mar. 15, 1999, Abstract.

Stinchcomb et al., "Isolation and Characterization of a Yeast Chromosomal Replicator", *Nature*, 282:39-43 (1979).

Straub, "A Case Against Heparin Therapy of Intravascular Coagulation", *Thrombos. Diathes. Haemorrh.*, 33:107-112 (1974).

Taylor et al., "DEGR-Factor Xa Blocks Disseminated Intravascular Coagulation Initiated by *Escherichia coli* Without Preventing Shock or Organ Damage", *Blood*, 78:364-368 (1991).

Taylor et al., "Lethal *E. coli* Septic Shock is Prevented by Blocking Tissue Factor With Monoclonal Antibody", *Circulatory Shock*, 33:127-134 (1991).

Taylor, "Baboon Model of *E. coli* Sepsis: Summary of Staging, Mechanism, and Diagnostic Markers", in *Molecular Aspects of Inflammation*, 42. Colloquium Mosbach, Springer-Verlag Berlin, pp. 277-288 (1991).

Tschumper et al., "Sequence of a Yeast DNA Fragment Containing a Chromosomal Replicator and the TRP1 Gene", *Gene*, 10:157-166 (1980).

Valentin et al., "Simultaneous Presence of Tissue Factor Pathway Inhibitor (TFPI) and Low Molecular Weight Heparin has a Synergistic Effect in Different Coagulation Assays", Blood *Coagulation Fibrinolysis*, 2:629-635 (1991).

Valentin et al., "Synergism Between Full Length TFPI and Heparin: Evidence for TFPI as an Important Factor for the Antithrombotic Activity of Heparin", *Blood Coagulation and Fibrinolysis*3:221-222 (1992).

Vallet, "Microthrombosis in Sepsis", *Minerva Anestesiol.*, 67(4):298-301 (Apr. 2001).

Van Solingen et al., "Fusion of Yeast Spheroplasts", J. Bact., 130:946-947 (1977).

Van der Poll et al., "Dose-Dependent Inhibition of Endotoxin-Induced Coagulation Activation by TFPI without Influencing the Fibrinolytic and Cytokine Response in Healthy Humans", ISTH (Aug. 14, 1999).

Warr et al., "Human Plasma Extrinsic Pathway Inhibitor Activity:II. Plasma Levels in Disseminated Intravascular Coagulation and Hepatocellular Disease", *Blood*, 74:994-998 (1989).

Warr et al., "Disseminated Intravascular Coagulation in Rabbits Induced by Administration of Endotoxin or Tissue Factor: Effect of Anti-Tissue Factor Antibodies and Measurement of Plasma Extrinsic Pathway Inhibitor Activity," *Blood*, 75:1481-1489 (1990).

Wherry et al., "Monoclonal Antibody to Human Tumor Necrosis Factor (TNF Mab): Multi-center Efficacy and Safety Study in Patients with the Sepsis Syndrome", at 33rd Interscience Conference on Antimicrobial Agents and Chemotherapy (ICAAC), New Orleans, Louisiana, Oct. 17-20, 1993.

Wun et al., "Cloning and Characterization of a cDNA Coding for the Lipoprotein-Associated Coagulation Inhibitor Shows That It Consists of Three Tandem Kunitz-type Inhibitory Domains", J. *Biological Chemistry*, 263:6001-6004 (1988).

Wun et al., "Immunoaffinity Purification and Characterization of Lipoprotein-Associated Coagulation Inhibitors from Hep G2 Hepatome, Chang Liver, and SK Hepatoma Cells," *J. Biol. Chem.*, 265:16096-16101 (1990).

Wun et al., "Comparison of Recombinant Tissue Factor Pathway Inhibitors Expressed in Human SK Hepatoma, Mouse C127, Baby Hamster Kidney, and Chinese Hamster Ovary Cells", *Thrombosis Haemostasis*, 68:54-59 (1992).

Yang et al., "Comparison of Methods for Local Delivery of Tissue Factor Pathway Inhibitor to Balloon-Injured Arteries in Rabbits" *Coron. Artery Dis.* 10(5):327-33 (Jul. 1999).

Zinsser, "The Action of Chemotherpeutic Agents", *MicroBiology*, 17th ed., W. Joklik et al., eds., pp. 235-277 (1980).

Supplementary Partial European Search Report dated Feb. 6, 2007 in the corresponding European Application No. EP 02 77 8529.4-2107.

Bajaj, M.S. et al., "Tissue Factor Pathway Inhibitor: Potential Therapeutic Applications," Thrombosis and Haemostasis, 78(1): 471-7 (1997) XP009064749.

Speich, E.I. et al., "Efficacy, Safety, and Tolerance of Piperacillin/ Tazobactam Compared to Co-Amoxiclav plus an Aminoglycoside in the Treatment of Severe Pneumonia," European Journal of Clinical Microbiology and Infectious Diseases, 17(5): 313-7 (May 1998) XP002416071.

\* cited by examiner

SEQUENCE LISTING

```
<160> NUMBER OF SEQ ID NOS: 2

<210> SEQ ID NO 1
<211> LENGTH: 276
<212> TYPE: PRT
<213> ORGANISM: Homo sapiens

<400> SEQUENCE: 1

Asp Ser Glu Glu Asp Glu Glu His Thr Ile Ile Thr Asp Thr Glu Leu
  1               5                   10                  15

Pro Pro Leu Lys Leu Met His Ser Phe Cys Ala Phe Lys Ala Asp Asp
                 20                  25                  30

Gly Pro Cys Lys Ala Ile Met Lys Arg Phe Phe Phe Asn Ile Phe Thr
             35                  40                  45

Arg Gln Cys Glu Glu Phe Ile Tyr Gly Gly Cys Glu Gly Asn Gln Asn
 50                  55                  60

Arg Phe Glu Ser Leu Glu Glu Cys Lys Lys Met Cys Thr Arg Asp Asn
 65                  70                  75                  80

Ala Asn Arg Ile Ile Lys Thr Thr Leu Gln Gln Glu Lys Pro Asp Phe
                 85                  90                  95

Cys Phe Leu Glu Glu Asp Pro Gly Ile Cys Arg Gly Tyr Ile Thr Arg
                100                 105                 110

Tyr Phe Tyr Asn Asn Gln Thr Lys Gln Cys Glu Arg Phe Lys Tyr Gly
            115                 120                 125

Gly Cys Leu Gly Asn Met Asn Asn Phe Glu Thr Leu Glu Glu Cys Lys
        130                 135                 140
```

```
Asn Ile Cys Glu Asp Gly Pro Asn Gly Phe Gln Val Asp Asn Tyr Gly
145                 150                 155                 160

Thr Gln Leu Asn Ala Val Asn Asn Ser Leu Thr Pro Gln Ser Thr Lys
            165                 170                 175

Val Pro Ser Leu Phe Glu Phe His Gly Pro Ser Trp Cys Leu Thr Pro
        180                 185                 190

Ala Asp Arg Gly Leu Cys Arg Ala Asn Glu Asn Arg Phe Tyr Tyr Asn
        195                 200                 205

Ser Val Ile Gly Lys Cys Arg Pro Phe Lys Tyr Ser Gly Cys Gly Gly
        210                 215                 220

Asn Glu Asn Asn Phe Thr Ser Lys Gln Glu Cys Leu Arg Ala Cys Lys
225                 230                 235                 240

Lys Gly Phe Ile Gln Arg Ile Ser Lys Gly Gly Leu Ile Lys Thr Lys
                245                 250                 255

Arg Lys Arg Lys Lys Gln Arg Val Lys Ile Ala Tyr Glu Glu Ile Phe
            260                 265                 270

Val Lys Asn Met
            275

<210> SEQ ID NO 2
<211> LENGTH: 277
<212> TYPE: PRT
<213> ORGANISM: Homo sapiens

<400> SEQUENCE: 2

Ala Asp Ser Glu Glu Asp Glu Glu His Thr Ile Ile Thr Asp Thr Glu
1               5                   10                  15

Leu Pro Pro Leu Lys Leu Met His Ser Phe Cys Ala Phe Lys Ala Asp
            20                  25                  30

Asp Gly Pro Cys Lys Ala Ile Met Lys Arg Phe Phe Phe Asn Ile Phe
        35                  40                  45

Thr Arg Gln Cys Glu Glu Phe Ile Tyr Gly Gly Cys Glu Gly Asn Gln
    50                  55                  60

Asn Arg Phe Glu Ser Leu Glu Glu Cys Lys Lys Met Cys Thr Arg Asp
65                  70                  75                  80

Asn Ala Asn Arg Ile Ile Lys Thr Thr Leu Gln Gln Glu Lys Pro Asp
                85                  90                  95

Phe Cys Phe Leu Glu Glu Asp Pro Gly Ile Cys Arg Gly Tyr Ile Thr
            100                 105                 110

Arg Tyr Phe Tyr Asn Asn Gln Thr Lys Gln Cys Glu Arg Phe Lys Tyr
        115                 120                 125

Gly Gly Cys Leu Gly Asn Met Asn Asn Phe Glu Thr Leu Glu Glu Cys
    130                 135                 140

Lys Asn Ile Cys Glu Asp Gly Pro Asn Gly Phe Gln Val Asp Asn Tyr
145                 150                 155                 160

Gly Thr Gln Leu Asn Ala Val Asn Asn Ser Leu Thr Pro Gln Ser Thr
                165                 170                 175

Lys Val Pro Ser Leu Phe Glu Phe His Gly Pro Ser Trp Cys Leu Thr
            180                 185                 190

Pro Ala Asp Arg Gly Leu Cys Arg Ala Asn Glu Asn Arg Phe Tyr Tyr
        195                 200                 205

Asn Ser Val Ile Gly Lys Cys Arg Pro Phe Lys Tyr Ser Gly Cys Gly
    210                 215                 220

Gly Asn Glu Asn Asn Phe Thr Ser Lys Gln Glu Cys Leu Arg Ala Cys
225                 230                 235                 240
```

```
               Lys Lys Gly Phe Ile Gln Arg Ile Ser Lys Gly Gly Leu Ile Lys Thr
                           245                 250                 255

Lys Arg Lys Arg Lys Lys Gln Arg Val Lys Ile Ala Tyr Glu Glu Ile
                           260                 265                 270

Phe Val Lys Asn Met
                           275
```

TREATMENT OF SEVERE PNEUMONIA BY ADMINISTRATION OF TISSUE FACTOR PATHWAY INHIBITOR (TFPI)

CROSS-REFERENCE TO RELATED APPLICATION

This application claims priority to Provisional Application Ser. No. 60/328,806 filed Oct. 15, 2001, hereby incorporated by reference in its entirety.

FIELD OF THE INVENTION

The present invention relates to a method for therapeutically treating severe pneumonia. More specifically, it relates to administering a tissue factor pathway inhibitor protein to attenuate exuberant or amplified physiological pathways associated with severe pneumonia.

BACKGROUND OF THE INVENTION

Pneumonia results from an acute infection of one or more functional elements of the lung, including alveolar spaces and interstitial tissue. In the USA, about 2 million people develop pneumonia each year, and 40,000 to 70,000 of these people die. Pneumonia ranks sixth among all disease categories as a cause of death and is the most common lethal nosocomial (hospital-acquired) infection. Community-acquired pneumonia (CAP) has a significant impact on health care costs in the United States, accounting for an estimated $14 billion per year in direct costs and $9 billion in lost wages. (Lynch J P, Martinez F J. *Community-acquired pneumonia*. Curr Opin Pulm Med. 1998; 4:162-172). In developing countries, lower respiratory tract infections typically are either the major cause of death or rank second only to infectious diarrhea. (*The Merck Manual*, Sec. 6, Ch. 73, Pneumonia, 2000).

The condition known as "severe pneumonia" is characterized according to guidelines set forth by various organizations, including the American Thoracic Society (ATS). (Am J Respir Crit Care Med 2001; 163:1730-1754). For example, the ATS requires at least one major criterion, such as a need for mechanical ventilation or septic shock, in addition to other criteria for a diagnosis of severe pneumonia. Generally, severe pneumonia can result from acute lung disease, lung inflammatory disease, or any perturbations in lung function due to factors such as inflammation or coagulation. A diagnosis of severe CAP is based on a patient being admitted to an ICU specifically for pneumonia. Epidemiologically, this patient population comprises approximately 10% of all ICU admissions. Patients in the ICU with pneumonia have the highest mortality of all CAP patients (30% to 40%) compared with less than 15% for general hospitalized patients with CAP.

Each year in the United States, community-acquired pneumonia (CAP) is diagnosed in approximately 4 million adults, with as many as 600,000 requiring hospitalization. Fine et al., *N. Engl. J. Med.* 336, 243-50, 1997. Overall, the incidence of CAP increases with age, with the greatest prevalence found in those aged 65 years and older. Marston et al., *Arch Intern Med.* 1997; 157:1709-1718. The incidence is also increased in patients with comorbidities, such as chronic obstructive pulmonary disease, asthma, diabetes mellitus, alcoholism, immunosuppression, renal insufficiency, chronic liver disease, and cardiac disease. Marrie, *Curr Opin Pulm Med.* 1996; 2:192-197; Niedermann et al., *Am Rev Respir Dis.* 1993; 148:1418-1426.

Pneumonia is the leading cause of death from infection in the United States and the sixth leading cause of death overall. The pneumonia-related mortality rate increased by 22% from 1979 to 1992, with elderly patients (65 years and older) accounting for 89% of all pneumonia-related deaths in 1992. See Pneumonia and influenza death rates—United States, 1979-1994 [published correction appears in *MMWR*. 1995; 44:782]. *MMWR*. 1995; 44:535-537. Fine and colleagues (1997) reported that certain coexisting illnesses (neoplastic disease, congestive heart failure (CHF) cerebrovascular disease, renal disease, and liver disease) and certain physical examination findings (altered mental status, increased heart rate, increased respiratory rate, decreased systolic blood pressure, and abnormally low or elevated temperatures) are also associated with increased CAP-related mortality. In addition, CAP has a significant impact on health care costs in the United States, accounting for an estimated $14 billion per year in direct costs and $9 billion in lost wages. Lynch & Martinez, *Curr Opin Pulm Med.* 1998; 4:162-172.

Tissue factor pathway inhibitor (TFPI) is a protein and a serine protease inhibitor present in mammalian blood plasma. Thomas, *Bull. Johns Hopkins Hosp.* 81, 26 (1947); Schneider, *Am. J. Physiol.* 149, 123 (1947); Broze & Miletich, *Proc. Natl. Acad. Sci. USA* 84, 1886 (1987). TFPI is also known as tissue factor inhibitor, tissue thromboplastin inhibitor, Factor III inhibitor, extrinsic pathway inhibitor (EPI), and lipoprotein-associated coagulation inhibitor (LACI). The name "tissue factor pathway inhibitor" (TFPI) was accepted by the International Society on Thrombosis and Hemostasis on Jun. 30, 1991.

Blood coagulation activation is the conversion of fluid blood to a solid gel or clot. In addition, consumption of the coagulation proteases leads to excessive bleeding. The main event is the conversion of soluble fibrinogen to insoluble strands of fibrin, although fibrin itself forms only 0.15% of the total blood clot. This conversion is the last step in a complex enzyme cascade. The components (factors) are present as zymogens, inactive precursors of proteolytic enzymes, which are converted into active enzymes by proteolytic cleavage at specific sites. Activation of a small amount of one factor catalyzes the formation of larger amounts of the next, and so on, resulting in an amplification that results in an extremely rapid formation of fibrin.

Coagulation is believed to be initiated by vessel damage which exposes factor VIIa to tissue factor (TF), which is expressed on cells beneath the endothelium. The factor VIIa-TF complex cleaves factor X to factor Xa and cleaves factor IX to factor IXa. TFPI binds to both factor VIIa and factor Xa. The complex formed between TFPI, factor VIIa (with its bound TF), and factor Xa inhibits further formation of factors Xa and IXa, required for sustained hemostasis. Broze, Jr., Ann. Rev. Med. 46:103 (1995).

Activation of the coagulation cascade by bacterial products, including endotoxins, introduced directly into the bloodstream can result in extensive fibrin deposition on arterial surfaces, as well as depletion of fibrinogen, prothrombin, factors V and VIII, and platelets. In addition, the fibrinolytic system is stimulated, resulting in further formation of fibrin degradation products.

At the same time as coagulation activation is apparently initiated by bacterial products (e.g., endotoxin), contravening mechanisms also appear to be activated by clotting, namely activation of the fibrinolytic system. Activated Factor XIII converts plasminogen pro-activator, to plasminogen activator that subsequently converts plasminogen to plasmin, thereby mediating clot lysis. The activation of plasma fibrinolytic systems may therefore also contribute to bleeding tendencies.

Endotoxemia is associated with an increase in the circulating levels of tissue plasminogen activator inhibitor (PAI). This inhibitor rapidly inactivates tissue plasminogen activator (TPA), thereby hindering its ability to promote fibrinolysis through activation of plasminogen to plasmin. Impairment of fibrinolysis may cause fibrin deposition in blood vessels, thus contributing to the DIC associated with septic shock.

Efforts are ongoing to identify satisfactory interventions for the prevention or treatment of severe pneumonia and associated coagulopathies. An agent that interrupts the coagulation pathway is not necessarily effective as a therapeutic or a prophylactic treatment of severe pneumonia. For example, heparin is a commonly used anticoagulant. However, management of the use of heparin has been difficult because heparin can induce excessive bleeding and has been found to attenuate coagulation abnormalities but not offer a survival benefit. See for example, Aoki et al., "A Comparative Double-BLIND randomized Trial of Activated Protein C and Unfractionated Heparin in the Treatment of Disseminated Intravascular Coagulation," *Int. J. Hematol.* 75, 540-47 (2002). Several clinical trials, mainly in meningococcal endotoxemia where fulminating DIC is a prominent feature, have failed to demonstrate reduction of mortality in sepsis by heparin treatment. See, for example, Corrigan et al., "Heparin Therapy in Septacemia with Disseminated Intravascular Coagulation. Effect on Mortality and on Correction of Hemostatic Defects," N. Engl. J. Med., 283:778-782 (1970); Lasch et al., Heparin Therapy of Diffuse Intravascular Coagulation (DIC)", Thrombos. Diathes. Haemorrh., 33:105 (1974); Straub, "A Case Against Heparin Therapy of Intravascular Coagulation", Thrombos. Diathes. Haemorrh., 33:107 (1974).

Administration of recombinant human ala-TFPI (a TFPI analog) has been shown to improve survival rates in animal models of sepsis. See, e.g., U.S. Pat. No. 6,063,764. As an endogenous protein, TFPI is well tolerated. TFPI administration by intravenous infusion or subcutaneous injection has been shown to reduce clotting ability, which is manifested as increased prothrombin time (PT). In studies of animals and humans, prolongations of PT were linearly related to the increase of plasma TFPI. A. A. Creasey, Sepsis 3:173 (1999).

There remains a need in the art for treatment approaches that will inhibit the lethal effects of severe pneumonia and simultaneously minimize potentially serious side effects.

SUMMARY OF THE INVENTION

One embodiment of the present invention is a method of treating or preventing severe pneumonia comprising administering TFPI or a TFPI analog to a patient who has or is at risk of developing severe pneumonia. In some embodiments, the patient has a demonstrable infection.

Another embodiment of the present invention is a method for treating severe pneumonia, comprising administering to a patient a continuous intravenous infusion of an agent selected from the group consisting of TFPI or a TFPI analog. In some embodiments, the patient has a demonstrable infection.

Other embodiments include any of the above embodiments wherein said TFPI or TFPI analog is administered by continuous intravenous infusion at a dose rate equivalent to administration of reference ala-TFPI at a dose rate of less than about 0.66 mg/kg/hr. In a preferred embodiment, said dose rate is equivalent to administration of reference ala-TFPI at a dose rate from about 0.00025 to about 0.050 mg/kg/hr. In a more preferred embodiment said dose rate is equivalent to administration of reference ala-TFPI at a dose rate from about 0.010 to about 0.045 mg/kg/hr. In a still more preferred embodiment, said TFPI or said TFPI analog is administered at a dose rate equivalent to administration of reference ala-TFPI at a dose rate of about 0.025 mg/kg/hr. In another preferred embodiment, said dose rate is administered to provide a total dose equivalent to administration of reference ala-TFPI at a total dose from about 0.024 to about 4.8 mg/kg. In another preferred embodiment, said dose rate is administered to provide a daily dose equivalent to administration of reference ala-TFPI at a daily dose of at least about 0.006 mg/kg and less than about 1.2 mg/kg.

Other embodiments include any of the above embodiments, wherein and said TFPI or TFPI analog is administered for at least 72 hours. In a preferred embodiment, said TFPI or TFPI analog is administered for at least 96 hours.

Other embodiments include any of the above embodiments wherein said TFPI analog is non-glycosylated ala-TFPI.

Other embodiments include any of the above embodiments wherein said TFPI analog comprises a first Kunitz domain consisting of amino acids 19-89 of SEQ ID NO:1. In a preferred embodiment, said TFPI analog further comprises a second Kunitz domain consisting of amino acids 90-160 of SEQ ID NO:1.

Other embodiments include any of the above embodiments wherein said TFPI analog comprises amino acids 1-160 of SEQ ID NO:1 or wherein said TFPI analog comprises a second Kunitz domain consisting of amino acids 90-160 of SEQ ID NO:1.

Other embodiments include any of the above embodiments wherein said TFPI or TFPI analog is prepared from a lyophilized composition comprising TFPI or a TFPI analog.

Other embodiments include any of the above embodiments wherein said TFPI or TFPI analog is administered as a formulation comprising arginine.

Other embodiments include any of the above embodiments wherein said TFPI or TFPI analog is administered as a formulation comprising citrate.

Other embodiments include any of the above embodiments wherein said TFPI or TFPI analog has a concentration of about 0.15 mg/ml in a formulation comprising about 300 mM arginine hydrochloride and about 20 mM sodium citrate and having a pH of about 5.5.

Other embodiments include any of the above embodiments, further comprising administering at the same time as, or within 24 hours of administering said TFPI or TFPI analog, an additional agent selected from the group consisting of an antibiotic, an antibody, an endotoxin antagonist, a tissue factor analog having anticoagulant activity, an immunostimulant, a cell adhesion blocker, heparin, BPI protein, an IL-1 antagonist, pafase (PAF enzyme inhibitor), a TNF inhibitor, an IL-6 inhibitor, and an inhibitor of complement. In a preferred embodiment, said additional agent is an antibody that binds specifically to an antigen selected from the group consisting of TNF, IL-6, and M-CSF.

Further embodiments of the present invention are apparent in view of the below-referenced drawings in conjunction with the detailed description.

DETAILED DESCRIPTION OF THE INVENTION

Administration of TFPI or analogs of TFPI is effective in the prophylaxis and treatment of severe pneumonia. Continuous low dosage administration of TFPI or analogs of TFPI (hereinafter "low dose TFPI administration") also is effective in the prophylaxis and treatment of severe pneumonia. TFPI or TFPI analog administration, particularly low dose administration, inhibits or attenuates acute or chronic inflammation, particularly severe pneumonia. When low dose TFPI administration is continued for at least three days, the risk of death from severe pneumonia is reduced, while the rate of complications from adverse side effects, particularly bleeding disorders, may be minimized. A further advantage of low dose TFPI administration is the avoidance of tolerance effects that, at sufficiently high doses, can reduce the plasma concentration of TFPI. Tolerance effects are stimulated half-maximally at a plasma TFPI concentration of about 850 ng/ml, whereas with low dose TFPI administration plasma levels generally stay below 500 ng/ml. Low dose TFPI administration generally is carried out by continuous intravenous infusion of TFPI or an analog of TFPI.

TFPI and TFPI Analogs

"TFPI" as used herein refers to the mature serum glycoprotein having the 276 amino acid residue sequence shown in SEQ ID NO:1 and a molecular weight of about 38,000 Daltons. It is a natural inhibitor of tissue factor activity and thus coagulation activation. U.S. Pat. No. 5,110,730 describes tissue factor (TF), and U.S. Pat. No. 5,106,833 describes TFPI. The cloning of the TFPI cDNA is described in Wun et al., U.S. Pat. No. 4,966,852. TFPI is a protease inhibitor and has 3 Kunitz domains, two of which are known to interact with factors VII and Xa respectively. The function of the third domain remains unknown. TFPI is believed to function in viva to limit the initiation of coagulation by forming an inert, quaternary factor $X_a$:TFPI:factor $VII_a$:tissue factor complex. See reviews by Rapaport, Blood 73:359-365 (1989) and Broze et al., Biochemistry 29:7539-7546 (1990). Many of the structural features of TFPI can be deduced from its homology with other well-studied protease inhibitors. TFPI is not an enzyme, so it probably inhibits its protease target in a stoichiometric manner, i.e., one of the Kunitz domains of TFPI inhibits one protease molecule. Preferably, Kunitz domains 1 and/or 2 will be present in TFPI molecules of the instant invention. The function of Kunitz domain 3 is unknown.

A "TFPI analog" is a derivative of TFPI modified with one or more amino acid additions or substitutions (generally conservative in nature), one or more amino acid deletions (e.g., TFPI fragments), or the addition of one or more chemical moieties to one or more amino acids, so long as the modifications do not destroy TFPI biological activity. Methods for making polypeptide analogs are known in the art and are described further below. A preferred TFPI analog is N-L-alanyl-TFPI (ala-TFPI), whose amino acid sequence is shown in SEQ ID NO:2. TFPI analogs possess some measure of the activity of TFPI as determined by a bioactivity assay as described below. A preferred bioactivity assay for TFPI and analogs is the prothrombin time (PT) assay (see below).

TFPI and TFPI analogs can be either glycosylated or non-glycosylated. Analogs of TFPI are described in U.S. Pat. No. 5,106,833. Ala-TFPI is a TFPI analog that is also known under the international drug name "tifacogin." Ala-TFPI includes the entire amino acid sequence of mature, full-length human TFPI plus an additional alanine residue at the amino terminus. The amino terminal alanine residue of ala-TFPI was engineered into the TFPI sequence to improve E. coli expression and to effect cleavage of what would otherwise be an amino terminal methionine residue. See U.S. Pat. No. 5,212,091.

Particularly preferred TFPI analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, and tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 1-70 conservative or non-conservative amino acid substitutions, such as 1, 2, 3, 4, 5, 6-50, 15-25, 5-10, or any integer from 1 to 70, so long as the desired function of the molecule remains intact. One of skill in the art may readily determine regions of the molecule of interest that can be modified with a reasonable likelihood of retaining biological activity as defined herein.

"Homology" refers to the percent similarity between two polynucleotide or two polypeptide moieties. Two polypeptide sequences are "substantially homologous" to each other when the sequences exhibit at least about 50%, preferably at least about 75%, more preferably at least about 80%-85%, preferably at least about 90%, and most preferably at least about 95%-98% sequence homology, or any percent homology between the specified ranges, over a defined length of the molecules. As used herein, "substantially homologous" also refers to sequences showing complete identity to the specified polypeptide sequence.

In general, "identity" refers to an exact amino acid-to-amino acid correspondence of two polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100.

Preferably, naturally or non-naturally occurring TFPI analogs have amino acid sequences which are at least 70%, 80%, 85%, 90% or 95% or more homologous to TFPI derived from SEQ ID NO:1. More preferably, the molecules are 98% or 99% homologous. Percent homology is determined using the Smith-Waterman homology search algorithm using an affine gap search with a gap open penalty of 12 and a gap extension penalty of 2, and a BLOSUM matrix of 62. The Smith-Waterman homology search algorithm is taught in Smith and Waterman, Adv. Appl. Math. 2:482-489 (1981).

The biological activity of TFPI and TFPI analogs can be determined by the prothrombin assay. Suitable prothrombin assays are described in U.S. Pat. No. 5,888,968 and in WO 96/40784. Briefly, prothrombin time can be determined using a coagulometer (e.g., Coag-A-Mate MTX II from Organon Teknika). A suitable assay buffer is 100 mM NaCl, 50 mM Tris adjusted to pH 7.5, containing 1 mg/ml bovine serum albumin. Additional reagents required are normal human plasma (e.g., "Verify 1" by Organon Teknika), thromboplastin reagent (e.g., "Simplastin Excel" by Organon Teknika), and TFPI standard solution (e.g., 20 µg of 100% pure ala-TFPI (or equivalent thereof) per ml of assay buffer). A standard curve is obtained by analyzing the coagulation time of a series of dilutions of the TFPI standard solution, e.g., to final concentrations ranging from 1 to 5 µg/ml. For the determination of clotting time, the sample or TFPI standard is first diluted into the assay buffer. Then normal human plasma is added. The clotting reaction is started by the addition of thromboplastin reagent. The instrument then records the clotting time. A linear TFPI standard curve is obtained from a plot of log clotting time vs. log TFPI concentration. The standard curve is adjusted based on the purity of the TFPI standard to correspond to the equivalent TFPI concentration of a 100% pure standard. For example, if the standard is a preparation of ala-TFPI that is 97% biochemically pure (i.e., it contains 3% by weight of molecular species without biological activity of TFPI), then the concentration of each dilution of the standard is multiplied by 0.97 to give the actual concentration of TFPI. Thus, a TFPI standard that is 1.0 µg/ml based on the actual weight per ml of a preparation that is 97% pure will be equivalent to, and treated as, a concentration of 1.0×0.97, or 0.97 µg/ml.

Obtaining TFPI and TFPI Analogs

TFPI and analogs of TFPI used in the methods of the invention can be isolated and purified from cells or tissues, chemically synthesized, or produced recombinantly in either prokaryotic or eukaryotic cells.

TFPI can be isolated by several methods. For example, cells that secrete TFPI include aged endothelial cells, young endothelial cells that have been treated with TNF for about 3 to 4 days, hepatocytes, and hepatoma cells. TFPI can be purified by conventional methods, including the chromatographic methods of Pedersen et al., 1990, *J. Biol. Chem.* 265, 16786-93, Novotny et al., 1989, *J. Biol. Chem.* 264, 18832-37, Novotny et al., 1991, *Blood* 78, 394-400, Wun et al., 1990, *J. Biol. Chem.* 265, 16096-101, and Broze et al., 1987, *Proc. Natl. Acad. Sci. USA* 84, 1886-90. TFPI appears in the bloodstream and can be purified from blood, see Pedersen et al., 1990.

A TFPI or TFPI variant can be produced using chemical methods to synthesize its amino acid sequence, such as by direct peptide synthesis using solid-phase techniques (Merrifield, *J. Am. Chem. Soc.* 85, 2149-2154, 1963; Roberge et al., *Science* 269, 202-204, 1995). Protein synthesis can be performed using manual techniques or by automation. Automated synthesis can be achieved, for example, using Applied Biosystems 431A Peptide Synthesizer (Perkin Elmer). Optionally, fragments of TFPI or TFPI variants can be separately synthesized and combined using chemical methods to produce a full-length molecule.

TFPI and TFPI analogs may be produced recombinantly as shown in U.S. Pat. No. 4,966,852. For example, the cDNA for the desired protein can be incorporated into a plasmid for expression in prokaryotes or eukaryotes. U.S. Pat. No. 4,847,201 provides details for transforming microorganisms with specific DNA sequences and expressing them. There are many other references known to those of ordinary skill in the art that provide details on expression of proteins using microorganisms. Many of those are cited in U.S. Pat. No. 4,847,201, such as Maniatas et al., 1982, Molecular Cloning, Cold Spring Harbor Press.

A variety of techniques are available for transforming microorganisms and using them to express TFPI and TFPI analogs. The following are merely examples of possible approaches. TFPI DNA sequences must be isolated and connected to the appropriate control sequences. TFPI DNA sequences are shown in U.S. Pat. No. 4,966,852 and can be incorporated into a plasmid, such as pUNC13 or pBR3822, which are commercially available from companies such as Boehringer-Mannheim. Once the TFPI DNA is inserted into a vector, it can be cloned into a suitable host. The DNA can be amplified by techniques such as those shown in U.S. Pat. No. 4,683,202 to Mullis and U.S. Pat. No. 4,683,195 to Mullis et al. TFPI cDNA may be obtained by inducing cells, such as hepatoma cells (such as HepG2 and SKHep) to make TFPI mRNA, then identifying and isolating the mRNA and reverse transcribing it to obtain cDNA for TFPI. After the expression vector is transformed into a host such as *E. coli*, the bacteria may be fermented and the protein expressed. Bacteria are preferred prokaryotic microorganisms and *E. coli* is especially preferred. A preferred microorganism useful in the present invention is *E. coli* K-12, strain MM294 deposited with the ATCC on Feb. 14, 1984 (Accession No. 39607), under the provisions of the Budapest Treaty.

It is also, of course, possible to express genes encoding polypeptides in eukaryotic host cell cultures derived from multicellular organisms. See, for example, Tissue Culture, 1973, Cruz and Patterson, eds., Academic Press. Useful mammalian cell lines include murine myelomas N51, VERO, HeLa cells, Chinese hamster ovary (CHO) cells, COS, C127, Hep G2, and SK Hep. TFPI and TFPI analogs can also be expressed in baculovirus-infected insect cells (see also U.S. Pat. No. 4,847,201, referred to above). See also Pedersen et al., 1990, J. of Biological Chemistry, 265:16786-16793. Expression vectors for eukaryotic cells ordinarily include promoters and control sequences compatible with mammalian cells such as, for example, the commonly used early and later promoters from Simian Virus 40 (SV40) (Fiers, et al., 1978, Nature, 273:113), or other viral promoters such as those derived from polyoma, Adenovirus 2, bovine papilloma virus, or avian sarcoma viruses, or immunoglobulin promoters and heat shock promoters. General aspects of mammalian cell host system transformations have been described by Axel, U.S. Pat. No. 4,399,216. It now appears also that "enhancer" regions are important in optimizing expression; these are, generally, sequences found upstream of the promoter region. Origins of replication may be obtained, if needed, from viral sources. However, integration into the chromosome is a common mechanism for DNA replication in eukaryotes. Plant cells are also now available as hosts, and control sequences compatible with plant cells such as the nopaline synthase promoter and polyadenylation signal sequences (Depicker, A., et al., 1982, J. Mol. Appl. Gen., 1:561) are available. Methods and vectors for transformation of plant cells have been disclosed in WO 85/04899.

Methods which can be used for purification of TFPI and TFPI analogs expressed in mammalian cells include sequential application of heparin-Sepharose, MonoQ, MonoS, and reverse phase HPLC chromatography. See Pedersen et al., supra; Novotny et al., 1989, J. Biol. Chem. 264:18832-18837; Novotny et al., 1991, Blood, 78:394-400; Wun et al., 1990, J. Biol. Chem. 265:16096-16101; Broze et al., 1987, PNAS (USA), 84:1886-1890; U.S. Pat. No. 5,106,833; and U.S. Pat. No. 5,466,783. These references describe various methods for purifying mammalian produced TFPI.

TFPI also can be expressed as a recombinant glycosylated protein using mammalian cell hosts, such as mouse C127 cells (Day et al., *Blood* 76, 1538-45, 1990), baby hamster kidney cells (Pedersen et al., 1990), Chinese hamster ovary cells, and human SK hepatoma cells. C127 TFPI has been used in animal studies and shown to be effective in the inhibition of tissue factor-induced intravascular coagulation in rabbits (Day et al., supra), in the prevention of arterial reocclusion after thrombolysis in dogs (Haskel et al., Circulation 84:821-827 (1991)), and in reduction of mortality in an *E. coli* sepsis model in baboons (Creasey et al., J. Clin. Invest. 91:2850 (1993)). Ala-TFPI can be expressed as a recombinant non-glycosylated protein using *E. coli* host cells. Methods have been described which yield a highly active ala-TFPI by in vitro refolding of the recombinant protein produced in *E. coli*. See, e.g., WO 96/40784.

TFPI and TFPI analogs also can be produced in bacteria or yeast and subsequently purified. Generally, the procedures shown in U.S. Pat. Nos. 5,212,091; 6,063,764; and 6,103,500 or WO 96/40784 can be employed. Ala-TFPI and other TFPI analogs can be purified, solubilized, and refolded according WO 96/40784 and Gustafson et al., Prot. Express. Pur. 5:233 (1994), which are incorporated herein by reference. For example, when prepared according Example 9 of WO 96/40784, preparations of ala-TFPI may be obtained that contain from about 85% to 90% of the total protein by weight as mature, properly-folded, biologically active ala-TFPI, about 10% to 15% of which has one or more oxidized methionine residues. These oxidized forms have biological activity that is equivalent to the biological activity of underivatized ala-TFPI, as determined by prothrombin assay, and are expected to be active in the invention disclosed herein. The remaining material comprises various modified forms of ala-TFPI, including dimerized, aggregated, and acetylated forms.

TFPI and TFPI analogs can have a significant number of cysteine residues, and the procedure shown in U.S. Pat. No. 4,929,700 is relevant to TFPI refolding. TFPI and analogs can be purified from the buffer solution by various chromatographic methods, such as those mentioned above. If desired, the methods shown in U.S. Pat. No. 4,929,700 may be employed. Any method may be employed to purify TFPI and TFPI analogs that results in a degree of purity and a level of activity suitable for administration to humans.

Therapeutic Methods and Compositions

Generally, TFPI and TFPI analogs are useful to treat or prevent those diseases that occur due to the up-regulation of tissue factor expression and hence TF activity brought on by TNF, IL-1 or other cytokines. TFPI administration, and particularly low dose TFPI administration, may lower the concentration of cytokines such as IL-6 in a patient. Low dose TFPI administration is useful for treating inflammation and coagulation abnormalities generally, including both acute and chronic inflammatory conditions such as severe pneumonia.

"Severe pneumonia" is defined according to the guidelines set forth by the American Thoracic Society. Specifically, severe pneumonia requires a diagnosis of pneumonia and the existence of either a) one of two major criteria, b) two of three minor criteria, or c) two of the four criteria from the British Thoracic Society (Thorax 2001; 56 [suppl IV]:1-64). The major criteria are 1) need for mechanical ventilation and 2) septic shock or need for pressors for >4 hours. The minor criteria are 1) systolic blood pressure$\leqq$90 mmHg, 2) multilobar pneumonia, and 3) hypoxemia criterion ($PaO_2$/$FiO_2$)<250. The criteria from the British Thoracic Society are 1) respiratory rate$\geqq$30 breaths/minute, 2) diastolic blood pressure$\leqq$60 mmHg, 3) blood urea nitrogen (BUN)>7.0 mM (>19.6 mg/dL) and 4) confusion. As is understood in the art, the hypoxemia criterion ($PaO_2$/$FiO_2$) refers to the partial pressure of arterial oxygen to the fraction of inspired oxygen and indicates the level of impairment of gas exchange.

Preferably, patients with severe pneumonia have an infection demonstrable by any means known in the art. These methods include, but are not limited to, detection of a pathogenic organism in a culture of blood or other normally sterile body fluid or tissue by, for example, GRAM stain, culture, histochemical staining, immunochemical assay, or nucleic acid assays. A demonstrable infection also can be evidenced by a chest radiograph consistent with a diagnosis of pneumonia that constitutes the reason for systemic anti-infective therapy, as well as any clinical symptom of infection, including, but not limited to, an increase in respiratory rate>/=30/min or $PaCO_2$/$FiO_2$<250, a decrease in blood pressure, and an increase in body temperature.

Formulations of TFPI and TFPI Analogs

Formulations of TFPI and TFPI analogs preferably are administered by intravenous infusions. Essentially continuous intravenous infusion is preferred. Methods to accomplish this administration are known to those of ordinary skill in the art. Infusion can be performed via a central line or a peripheral line. While large fluctuations in the dose rate are to be avoided, short-term deviations from the dose rates of the invention are acceptable provided the resulting plasma level of administered TFPI is within 20% of that expected from a continuous infusion at a constant dose rate according to the preferred embodiments of invention.

Before administration to patients, formulants may be added to TFPI and TFPI analogs. A liquid formulation is preferred. TFPI and TFPI analogs may be formulated at different concentrations, using different formulants, and at any physiologically suitable pH compatible with the route of administration, solubility, and stability of the TFPI protein. A preferred formulation for intravenous infusion includes ala-TFPI at up to about 0.6 mg/ml, arginine hydrochloride at up to 300 mM, and sodium citrate buffer at pH 5.0-6.0. Certain solutes such as arginine, NaCl, sucrose, and mannitol serve to solubilize and/or stabilize ala-TFPI. See WO 96/40784. An especially preferred formulation for intravenous infusion contains about 0.15 mg/ml ala-TFPI, 300 mM arginine hydrochloride, and 20 mM sodium citrate at pH 5.5. TFPI and TFPI analogs also can be formulated at concentrations up to about 0.15 mg/ml in 150 mM NaCl and 20 mM sodium phosphate or another buffer at pH 5.5-7.2, optionally with 0.005% or 0.01% (w/v) polysorbate 80 (Tween 80). Other formulations contain up to about 0.5 mg/ml TFPI, or TFPI analog in 10 mM sodium acetate at pH 5.5 containing either 150 mM NaCl, 8% (w/v) sucrose, or 4.5% (w/v) mannitol. TFPI and TFPI analogs can also be formulated at higher concentrations up to several mg/ml using high salt. For example, one formulation contains up to about 6.7 mg/ml ala-TFPI in 500 mM NaCl and 20 mM sodium phosphate at pH 7.0.

Further examples of formulants for TFPI and TFPI analogs include oils, polymers, vitamins, carbohydrates, amino acids, salts, buffers, albumin, surfactants, or bulking agents. Preferably carbohydrates include sugar or sugar alcohols such as mono, di, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxyethyl starch and carboxymethylcelloluose, or mixtures thereof. Sucrose is most preferred. Sugar alcohol is defined as a $C_4$ to $C_8$ hydrocarbon having an —OH group and includes galactitol, inositol, mannitol, xylitol, sorbitol, glycerol, and arabitol. Mannitol is most preferred. These sugars or sugar alcohols mentioned above may be used individually or in combination. There is no fixed limit to the amount used as long as the sugar or sugar alcohol is soluble in the aqueous preparation. Preferably, the sugar or sugar alcohol concentration is between 1.0 w/v % and 7.0 w/v %, more preferable between 2.0 and 6.0 w/v %.

Preferably amino acids include levorotary (L) forms of carnitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. It is also preferred to use a buffer in the composition to minimize pH changes in the solution before lyophilization or after reconstitution. Most any physiological buffer may be used, but citrate, phosphate, succinate, and glutamate buffers or mixtures thereof are preferred. Preferably, the concentration of the buffer is from 0.01 to 0.3 molar. Surfactants that can be added to the formulation are shown in EP Nos. 270,799 and 268,110.

Additionally, TFPI and TFPI analogs can be chemically modified, for example by covalent conjugation to a polymer to increase its circulating half-life. Preferred polymers and methods to attach them to peptides are taught in U.S. Pat. Nos.

4,766,106, 4,179,337, 4,495,285, and 4,609,546. Preferred polymers are polyoxyethylated polyols and polyethylene glycol (PEG). PEG is soluble in water at room temperature and has the general formula: $R(O-CH_2-CH_2)_n-O-R$ where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1000 and 40,000, more preferably between 2000 and 20,000, most preferably between 3,000 and 12,000. Preferably, PEG has at least one hydroxy group, more preferably it is a terminal hydroxy group. It is this hydroxy group which is preferably activated to react with a free amino group on the inhibitor. However, it will be understood that the type and amount of the reactive groups may be varied to achieve a covalently conjugated PEG/TFPI of the present invention.

Water soluble polyoxyethylated polyols are also useful in the present invention. They include polyoxyethylated sorbitol, polyoxyethylated glucose, polyoxyethylated glycerol (POG), etc. POG is preferred. One reason is that the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in Knauf et al., 1988, J. Bio. Chem. 263:15064-15070, and a discussion of POG-protein conjugates is found in U.S. Pat. No. 4,766,106.

After a liquid pharmaceutical composition of TFPI or a TFPI analog is prepared, it can be lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) that may include additional ingredients. Upon reconstitution, the composition is preferably administered to subjects by continuous intravenous infusion.

Dosages of TFPI and TFPI Analogs

TFPI or TFPI analogs are administered at a concentration that is therapeutically effective to treat and prevent severe pneumonia. Such doses also are effective for other acute or chronic inflammations, and generally diseases in which cytokines upregulate tissue factor expression. To accomplish this goal, TFPI or TFPI analogs preferably are administered intravenously. Methods to accomplish this administration are known to those of ordinary skill in the art. Generally, TFPI or TFPI analogs are given at a dose between 1 μg/kg and 20 mg/kg, more preferably between 20 μg/kg and 15 mg/kg, most preferably between 1 and 10 mg/kg.

The above dosages are generally administered over a period of at least about 1 day, and usually several days, such that the total daily dose administered to a host in single or divided doses may be in amounts, for example, from about 2 to about 15 mg/kg body weight daily and preferably from about 4 to about 10 mg/kg. Dosage unit compositions may contain such amounts or submultiples thereof to make up the daily dose. Lower daily dosage amounts may be useful for prophylactic or other purposes, for example, from 1 μg/kg to 2 mg/kg. The amount of active ingredient that may be combined with the carrier materials to produce a single dosage form will vary depending upon the patient treated and the particular mode of administration.

The dosage regimen is selected in accordance with a variety of factors, including the type, age, weight, sex, diet and medical condition of the patient, the severity of the condition, the route of administration, pharmacological considerations such as the activity, efficacy, pharmacokinetic and toxicology profiles, whether a drug delivery system is utilized and whether the compound is administered as part of a drug combination. Thus, the dosage regimen actually employed may vary widely and therefore may deviate from the preferred dosage regimen set forth above. Preferably, doses of TFPI or TFPI analogs should not exceed a dose rate equivalent to a dose rate of ala-TFPI of about 0.66 mg/kg/hr.

Low Dose Administration

When TFPI or a TFPI analog is given at a dose rate equivalent to administration of ala-TFPI at a dose rate of at least about 0.00025 mg/kg/hr (0.00417 μg/kg/min) and less than about 0.050 mg/kg/hr (0.833 μg/kg/min), efficacy in treating severe pneumonia is retained and adverse side effects, such as bleeding, are minimized. For improved combined efficacy and safety, the dose rate preferably is equivalent to a dose rate of ala-TFPI of at least about 0.010 mg/kg/hr (0.167 μg/kg/min) and less than about 0.045 mg/kg/hr (0.833 μg/kg/min), or equivalent to a dose rate of ala-TFPI of at least about 0.020 mg/kg/hr and less than about 0.040 mg/kg/hr, and most preferably equivalent to a dose rate of ala-TFPI of about 0.025 mg/kg/hr (0.417 μg/kg/min)). The route of administration is generally by intravenous administration, with continuous intravenous infusion preferred. Infusion can be administered for at least about 72, 96, 120, or 240 hours. Preferably, continuous infusion is administered for 3 to 8 days, more preferably 3 to 6 days, and most preferably for about 4 days.

To administer "by continuous infusion" means that the infusion is maintained at approximately the prescribed rate without substantial interruption for most of the prescribed duration. Alternatively, intermittent intravenous infusion can be used. If intermittent infusion is used, then a time-averaged dose rate should be used which is equivalent to the dose rates described above for continuous infusion. In addition, the program of intermittent infusion must result in a maximum serum concentration not more than about 20% above the maximum concentration obtained using continuous infusion. To avoid adverse reactions in the patient, particularly side effects involving bleeding, the dose rate should be less than a dose rate that is equivalent to continuous intravenous infusion of ala-TFPI at about 0.050 mg/kg/hr.

All doses described herein, including dose rates and total doses, are subject to up to 10% variation in practice due to errors in determining protein concentration and biological activity with the prothrombin assay. Thus, any actually administered dose up to 10% higher or 10% lower than a dose stated herein is considered to be equivalent to the stated dose. For this reason, all doses have been stated as "about" a specific dose. For example, a dose described as "about 0.025 mg/kg/hr" is considered equivalent to any actual dose ranging from 0.0225 to 0.0275 mg/kg/hr.

A bolus injection or a briefly higher infusion rate of TFPI or an analog of TFPI may also be employed in the practice of the present invention if followed by low dose TFPI administration. For example, a bolus injection or higher infusion rate can be used to reduce the equilibration time of administered TFPI or TFPI analog in the circulation of a patient. In doing so, the eventual steady state plasma level of TFPI can be reached more rapidly and receptors for TFPI can be saturated faster. Administration of ala-TFPI to humans at about 0.025 mg/kg/hr for 2 hours increases plasma levels of TFPI (plus ala-TFPI) from about 80 ng/ml to about 125 ng/ml, or an increase of approximately 50%. The same level will be reached faster if the infusion rate is increased, or a bolus injection is used. Higher infusion rates will result in higher levels if infusion is continued until steady state is obtained. Steady state level for administration of ala-TFPI at about 0.050 mg/kg/hr was found to be about 300 ng/ml, and for administration of ala-TFPI at about 0.33 or about 0.66 mg/kg/hr was found to be about at least 2 μg/ml in patients suffering from sepsis.

Total daily dose administered to a host in a single continuous infusion or in divided infusion doses may be in amounts, for example, equivalent to administration of at least about 0.006 mg/kg/day to less than about 1.2 mg/kg/day of ala-TFPI, more usually equivalent to administration of from about 0.24 mg/kg/day to less than about 1.2 mg/kg/day of ala-TFPI, and preferably equivalent to about 0.6 mg/kg/day of ala-TFPI. Lower amounts within this range may be useful for prophylactic or other purposes. The dosing protocols of the invention can also be expressed as the total dose administered to the patient. The total dose is the mathematical product of the rate of infusion and the total time of infusion. For example, at the preferred dose rate of about 0.025 mg/kg/hr for ala-TFPI and the preferred infusion time of 96 hours, the total dose is about 2.4 mg ala-TFPI per kg body weight. The total dose of TFPI administered according to the invention is equivalent to at least about 0.75 µg/kg and less than about 4.8 mg/kg of ala-TFPI. Preferably the total dose is equivalent to at least about 1 mg/kg and less than about 4.8 mg/kg of ala-TFPI. More preferably the total dose is equivalent to about 2.4 mg/kg of ala-TFPI.

One factor that can be used to adjust the dosage regimen is the individual patient's coagulation function, which is typically measured using a prothrombin time (PT) assay, or the International Normalized Ratio (INR). INR is the standardization of the PT assay in which the assay is calibrated against an international reference thromboplastin reagent. See, e.g., R. S. Riley et al., J. Clin. Lab. Anal. 14:101-114 (2000). The INR response to ala-TFPI in healthy human volunteers is approximately linear over the range of plasma concentrations seen (FIG. 3). The overall change in INR is 1.2 units per 1 µg/ml increase of plasma ala-TFPI concentration.

In a pharmacodynamic model, the INR response to ala-TFPI is best described by a log-linear model in which log INR was linearly related to ala-TFPI plasma concentration. The log-linear nature of the response means that subjects with elevated INR at baseline are likely to experience greater anticoagulant responses than subjects with low baseline values who have similar levels of circulating ala-TFPI.

The dosing regimens described above, including dosing rate on a mg/kg/hr basis and total daily dose, are expressed as a dose "equivalent to administration of reference ala-TFPI." This means that they are determined quantitatively by normalization to a dose of "reference ala-TFPI" which is defined as mature, 100% pure (on a protein basis), properly folded, biologically active, non-glycosylated ala-TFPI. Ala-TFPI is an analog of TFPI whose amino acid sequence is depicted in SEQ ID NO:2. Other forms of TFPI can also be used in the invention, including mature, full-length TFPI and analogs thereof. To determine the appropriate dosing range for practicing the invention with forms of TFPI other than ala-TFPI and with preparations of ala-TFPI or another TFPI analog that are less than 100% pure, the dosing ranges described herein for reference ala-TFPI can be adjusted based on the intrinsic biological activity of the particular form of TFPI and further adjusted based on the biochemical purity of the preparation.

The intrinsic biological activity of TFPI or a TFPI analog refers to the specific activity, as defined by the prothrombin assay, of the mature, 100% pure, properly folded TFPI or TFPI analog. Thus, the equivalent dose is calculated as (reference ala-TFPI dose)/((relative intrinsic activity)×(biochemical purity)), where relative intrinsic activity refers to (intrinsic activity of analog)/(intrinsic activity of reference ala-TFPI). For example, if a particular TFPI analog has an intrinsic biological activity which is 80% that of reference ala-TFPI, then the equivalent dose for the particular TFPI analog are obtained by dividing the dose values for reference ala-TFPI by 0.8. Further, if the formulation administered to a patient is, for example, only 90% biochemically pure, i.e., comprising 10% of molecular species which lack biological activity of TFPI, then an additional correction of the reference dose values for ala-TFPI is performed by dividing the dose values by 0.9. Thus, for a hypothetical TFPI analog that has 80% of the intrinsic activity of ala-TFPI and is 90% biochemically pure as administered, a dose rate equivalent to administration of reference ala-TFPI at 0.025 mg/kg/hr would be 0.0347 mg/kg/hr (i.e., 0.025/(0.8×0.9)).

Equivalent doses can also be determined without knowing either intrinsic activity or biochemical purity by determining relative biological activity. Relative biological activity can be determined by comparing a particular TFPI analog to a TFPI biological activity standard using the prothrombin time assay. For example, ala-TFPI produced according to the method of Example 9 of WO 96/40784, which contains about 85% biologically active TFPI molecular species, can be used as a TFPI biological activity standard. Ala-TFPI produced according to the method of Example 9 of WO 96/40784 has about 85% of the activity of reference ala-TFPI in the prothrombin assay. In plotting a prothrombin time standard curve, the log of clotting time is plotted against the log of TFPI concentration. If the TFPI biological activity standard possesses 85% of the activity of reference ala-TFPI, then a standard curve can be prepared which is equivalent to that for reference ala-TFPI if the concentrations of the TFPI biological activity standard are multiplied by 0.85 prior to plotting, so that the activity plotted is equivalent to the activity of 100% pure reference ala-TFPI. When the clotting time for a particular TFPI analog is compared to the standard curve, the equivalent concentration of reference ala-TFPI can be read off the curve. Alternatively, if the slope of the linear portion of the standard curve is obtained by linear regression analysis, then the slope can be corrected based on the activity of the TFPI biological activity standard relative to reference ala-TFPI. The relative biological activity of a particular TFPI analog is thus equal to the ratio of reference ala-TFPI activity to the activity of the analog. For example, if a particular analog requires 1.43 µg to produce the same prothrombin time activity as 1.00 µg of reference ala-TFPI, then the relative biological activity of the analog is 1.00/1.43, or 0.7. For that analog, the equivalent dose to a reference ala-TFPI dose is obtained by dividing the reference ala-TFPI dose by the relative biological activity of the analog. For example, a 0.025 mg/kg/hr dose for reference ala-TFPI would be equivalent to 0.0357 mg/kg/hr of the analog (i.e., 0.025/0.7).

While TFPI or a TFPI analog can be administered as the sole active anticoagulation pharmaceutical agent, these molecules also can be used in combination with one or more additional therapeutic agents to provide a combination therapy for the treatment of sever pneumonia. Such additional therapeutic agents include antibodies such as, for example, anti-endotoxin, monoclonal antibodies (e.g., endotoxin-binding Mabs) and anti-TNF products such as an anti-TNF murine Mab. TFPI and TFPI analogs can also be combined with interleukin-1 receptor antagonists, bactericidal/permeability increasing (BPI) protein, immunostimulant, compounds having anti-inflammatory activity such as PAF antagonists, and cell adhesion blockers (e.g., antiplatelet agents such as GPIIb/IIIa inhibitors). When administered as a combination, the therapeutic agents can be formulated as separate compositions that are given at the same time or different times. Preferably, additional therapeutic agents are given either at the same time (i.e., during the administration period of TFPI or TFPI analogs) or within 24 hours of the administration period of TFPI or TFPI analogs (i.e., within 24 hours prior to the start of, or within 24 hours after the end of, the administration period of TFPI or TFPI analogs). Additional therapeutic agents can also be given as a single composition together with the TFPI or TFPI analogs.

TFPI or a TFPI analog also can be given in combination with other agents that would be effective to treat severe pneumonia. For example, the following may be administered in combination with TFPI or a TFPI analog: antibiotics that can treat the underlying bacterial infection, monoclonal antibodies that are directed against bacterial cell wall components, receptors that can complex with cytokines that are involved in the severe pneumonia pathway, and generally any agent or protein that can interact with cytokines or other activated or amplified physiological pathways including complement proteins to attenuate severe pneumonia and/or its symptoms.

Useful antibiotics include those in the general category of: beta-lactam rings (penicillin), amino sugars in glycosidic linkage (aminoglycosides), macrocyclic lactone rings (macrolides), polycyclic derivatives of napthacenecarboxanide (tetracyclines), nitrobenzene derivatives of dichloroacetic acid, peptides (bacitracin, gramicidin, and polymyxin), large rings with a conjugated double bond system (polyenes), sulfa drugs derived from sulfanilamide (sulfonamides), 5-nitro-2-furanyl groups (nitrofurans), quinolone carboxylic acids (nalidixic acid), and many others. Other antibiotics and more versions of the above specific antibiotics may be found in Encyclopedia of Chemical Technology, 3rd Edition, Kirk-Othymer (ed.), Vol. 2, pages 782-1036 (1978) and Vol. 3, pages 1-78, Zinsser, MicroBiology, 17th Edition W. Joldik et al. (Eds.) pages 235-277 (1980), or Dorland's Illustrated Medical Dictionary, 27th Edition, W. B. Saunders Company (1988).

Other agents that may be combined with TFPI or a TFPI analog include endotoxin antagonists such as E5531 (a Lipid A analog, see Asai et al., Biol. Pharm. Bull. 22:432 (1999)), TF analogs with anticoagulant activity (see, e.g., Kelley et al., Blood 89:3219 (1997) and Lee & Kelley, J. Biol. Chem. 273:4149 (1998)), monoclonal antibodies directed to cytokines, such as those monoclonal antibodies directed to IL-6 or M-CSF, see U.S. Ser. No. 07/451,218, filed Dec. 15, 1989, and monoclonal antibodies directed to TNF (see Cerami et al., U.S. Pat. No. 4,603,106), inhibitors of protein that cleave the mature TNF prohormone from the cell in which it was produced (see U.S. Ser. No. 07/395,253, filed Aug. 16, 1989), antagonists of IL-1 (see U.S. Ser. No. 07/517,276, filed May 1, 1990), inhibitors of IL-6 cytokine expression such as inhibin (see U.S. Pat. No. 5,942,220), and receptor based inhibitors of various cytokines such as IL-1. Antibodies to complement or protein inhibitors of complement, such as $CR_1$, DAF, and MCP also can be used.

All patents, patent applications, and references cited in this disclosure are incorporated herein by reference in their entireties.

The present invention will now be illustrated by reference to the following examples that set forth particularly advantageous embodiments. However, it should be noted that these embodiments are illustrative and are not to be construed as restricting the invention in any way.

EXAMPLES

Example 1 ala-TFPI Treatment of Severe Pneumonia Patients

Patients with severe pneumonia were evaluated to explore the potential affect of treatment with ala-TFPI in a relatively homogeneous group. Pneumonia patients were identified if one source of sepsis documented by the investigator was coded as pneumonia. Other sites of infection could also be present. Due to the difficulty in differentiating infectious from chemical sequelae, patients with aspiration pneumonia were not included. Patients identified as having pneumonia were then classified as being culture positive (any evidence of infection such as culture or Gram stain), or culture negative (negative culture or culture not done). Patients were treated by continuous intravenous confusion with a preparation of non-glycosylated ala-TFPI expressed in *E. coli* at a dose of 0.025 mg/kg/h formulated in a buffer containing 300 mM L-arginine, 20 mM sodium citrate, pH 5.5, osmolarity 560+/−110 mOsm. Placebo consisted of the same buffer without ala-TFPI and was infused at the same rate as the study drug. Results of these analyses demonstrate a positive effect from ala-TFPI treatment in those patients with culture positive pneumonia (Table 1). Those patients without evidence of an infectious source demonstrated a negative effect.

TABLE 1

Mortality by Pneumonia Status

| INR ≧ 1.2 | Overall | | |
|---|---|---|---|
| | Placebo | TFPI | p = |
| Pneumonia Culture Positive | | | |
| (N =) | 236 | 268 | |
| % Mortality | 39.8% | 31.3% | 0.05 |
| Pneumonia Culture Negative | | | |
| (N =) | 118 | 122 | |
| % Mortality | 30.5% | 45.1% | 0.02 |

TABLE 2

Mortality by Pneumonia Status Low INR

| INR < 1.2 | Overall | | |
|---|---|---|---|
| | Placebo | TFPI | p = |
| Pneumonia Culture Pos. | | | |
| (N =) | 33 | 22 | |
| % Mortality | 30.3% | 13.6% | 0.15 |
| Pneumonia Culture Neg. | | | |
| (N =) | 25 | 23 | |
| % Mortality | 32.0% | 8.7% | 0.08 |

The increased mortality in the high INR culture negative group appeared to be present in patient populations with or without added administration of heparin, although it should be noted that the number of subjects in the pneumonia culture negative, non-heparin group is relatively small (Table 3). A strong positive treatment effect was observed in the culture positive/no heparin cohort.

TABLE 3

Mortality by Pneumonia Status and Heparin

| INR >= 1.2 | Pneumonia Culture Positive | | | Pneumonia Culture Negative | | |
|---|---|---|---|---|---|---|
| | Placebo | TFPI | p = | Placebo | TFPI | p = |
| Heparin at Baseline or During Dosing | | | | | | |
| (N =) | 160 | 187 | | 87 | 85 | |
| % Mortality | 32.5% | 31.6% | 0.84 | 36.8% | 56.5% | 0.01 |
| No Heparin at Baseline or During Dosing | | | | | | |
| (N =) | 76 | 81 | | 31 | 37 | |
| % Mortality | 55.3% | 30.9% | 0.002 | 32.3% | 48.6% | 0.17 |

Example 2

Investigation of Baseline Severity of Illness Variables

A number of baseline severity of illness variables were evaluated to determine whether there were group imbalances that could explain the observed outcome. These data indicate that the difference in outcomes associated with culture status are not due to baseline imbalances. Accordingly, the results appear to represent a differential effect of TFPI treatment due to biological differences between patients with and without infection. Despite the fact that the severity indicators (e.g., APACHE II score or organ dysfunction score) were either equal to placebo or lower in the TFPI treated pneumonia culture negative group the culture negative group demonstrated the highest overall mortality (Table 4).

TABLE 4

Baseline Severity of Illness by Pneumonia Status

| INR >= 1.2 | Pneumonia Culture Positive | | Pneumonia Culture Negative | |
|---|---|---|---|---|
| | Placebo | TFPI | Placebo | TFPI |
| N = | 236 | 268 | 118 | 122 |
| % Mortality | 39.8% | 31.3% | 30.5% | 45.1% |
| APACHE II | 25.8 | 25.9 | 24.3 | 25.2 |
| INR | 1.53 | 1.50 | 1.52 | 1.45 |

TABLE 4-continued

Baseline Severity of Illness by Pneumonia Status

| INR >= 1.2 | Pneumonia Culture Positive | | Pneumonia Culture Negative | |
|---|---|---|---|---|
| | Placebo | TFPI | Placebo | TFPI |
| Mean Organ Dysfunctions | 3.0 | 3.0 | 3.0 | 2.9 |
| CV - Hypotension | 79% | 74% | 73% | 72% |
| Acidosis | 66% | 66% | 64% | 58% |
| Oliguria | 42% | 48% | 47% | 49% |
| Pulmonary Dysfunction | 93% | 91% | 91% | 90% |
| Thrombocytopenia | 20% | 23% | 22% | 16% |

IL-6 is an inflammatory cytokine that is elevated early in sepsis, reflects the intensity of the inflammatory response and is associated with outcome. At baseline, IL-6 levels are lower in patients clinically identified as having pneumonia but without evidence of infection (Table 5). This suggests that there is a biological difference between patients with a documented infectious source of pneumonia versus those without an apparent infectious source. Paradoxically, the culture negative TFPI group has the lowest baseline IL-6 levels but the highest mortality rate. In a sepsis population IL-6 levels fall over time. The rate of fall in IL-6 is reduced in TFPI treated pneumonia culture negative subjects (Table 5). This suggests that the biological effect of TFPI may differ in those patients with and without infection.

TABLE 5

IL-6 by Pneumonia Status

| INR ≧ 1.2 Pneumonia | Baseline | | | 6 hrs (% Δ*) | | | 24 hrs (% Δ*) | | | 96 hrs (% Δ*) | | |
|---|---|---|---|---|---|---|---|---|---|---|---|---|
| | PL | TFPI | p = | PL | TFPI | p = | PL | TFPI | p = | PL | TFPI | p = |
| Culture Positive (n = 493) | 494 | 489 | 0.96 | −25% | −27% | 0.75 | −57% | −63% | 0.26 | −83% | −84% | 0.69 |
| Culture Negative (n = 236) | 300 | 195 | 0.11 | −21% | −8% | 0.08 | −54% | −32% | 0.03 | −98% | −97% | 0.06 |

*% Δ = % change from baseline (geometric mean)

Example 3

Analysis of Severe Pneumonia Patients by Type of Documentation of Infection

As discussed above, an overall benefit from ala-TFPI treatment was observed in those patients with the highest certainty of infection, i.e., those with a positive blood culture. In an analysis of severe pneumonia patients by type of documentation of infection, a benefit from ala-TFPI treatment was seen in both subjects with a positive blood culture and those with other evidence (Table 6). The effect was strongest in the bacteremia group, i.e., the group with the highest probability of infection or most demonstrable source of infection.

TABLE 6

Mortality by Culture Status and Pneumonia Status

| INR ≧ 1.2 Pneumonia | Blood Culture Positive | | | Other Culture Positive | | | Culture Negative/ND | | |
|---|---|---|---|---|---|---|---|---|---|
| | Placebo | TFPI | p = | Placebo | TFPI | p = | Placebo | TFPI | p = |
| (N =) | 80 | 107 | | 156 | 161 | | 110 | 110 | |
| % Mortality | 38.8% | 26.2% | 0.07 | 40.4% | 34.8% | 0.30 | 30.9% | 46.4% | 0.02 |

As previously shown, patients with documentation of infection (blood+"other") benefited from TFPI treatment in the absence of heparin. This result is mostly due to the benefit derived from the pneumonia group (Table 7). This finding seems to indicate that the benefit from endogenous anticoagulants is greatest in those patients with severe pulmonary infections.

TABLE 7

Mortality by Infection Status, Pneumonia Status and Heparin Use

| | Heparin | | | No Heparin | | |
|---|---|---|---|---|---|---|
| INR ≧ 1.2 | Placebo | TFPI | p = | Placebo | TFPI | p = |
| Documented Infection (Blood + "Other") | | | | | | |
| N = | 433 | 442 | | 211 | 207 | |
| % Mortality | 31.4% | 31.9% | 0.89 | 43.1% | 32.4% | 0.02 |
| Pneumonia (Culture Positive) | | | | | | |
| N = | 160 | 187 | | 76 | 81 | |
| % Mortality | 32.5% | 31.6% | 0.84 | 55.3% | 30.9% | 0.002 |
| Non-Pneumonia Documented Infections (Documented minus Pneumonia) | | | | | | |
| N = | 273 | 255 | | 135 | 126 | |
| % Mortality | 30.8% | 32.2% | 0.73 | 36.3% | 33.3% | 0.62 |

To further limit heterogeneity, future trials can be focused on community acquired pneumonia (CAP). Patients who develop pneumonia while in hospital (nosocomial pneumonia) are more likely to be colonized with pathogenic organisms and have other pulmonary disorders making the diagnosis of infectious pneumonia more difficult. In addition, patients with CAP are less likely to have been exposed to heparin than patients with nosocomial pneumonia. When data were analyzed by length of stay in hospital prior treatment, a similar benefit was noted for culture positive patients hospitalized ≦2 days (community acquired) versus those hospitalized longer than 2 days (nosocomial). The negative effect in the culture negative patients was seen primarily in the nosocomial group (Table 8).

TABLE 8

Mortality by Pneumonia Status and Time from Hospitalization

| | Pneumonia Culture Positive | | | Pneumonia Culture Negative | | |
|---|---|---|---|---|---|---|
| INR ≧ 1.2 | Placebo | TFPI | p = | Placebo | TFPI | p = |
| Community Acquired (≦2 days) | | | | | | |
| (N =) | 121 | 143 | | 61 | 52 | |
| % Mortality | 38.8% | 29.4% | 0.10 | 27.9% | 30.8% | 0.74 |
| Nosocomial (>2 days) | | | | | | |
| (N =) | 115 | 125 | | 57 | 70 | |
| % Mortality | 40.9% | 33.6% | 0.24 | 33.3% | 55.7% | 0.01 |

The present invention has been described with reference to specific embodiments. However, this application is intended to cover those changes and substitutions which may be made by those skilled in the art without departing from the spirit and the scope of the appended claims.

What is claimed is:

1. A method of treating severe pneumonia comprising: administering TFPI or ala-TFPI to a patient who has severe pneumonia, wherein said patient has a demonstrable infection.

2. The method of claim 1 wherein said ala-TFPI is non-glycosylated.

3. The method of claim 1 wherein said TFPI or ala-TFPI is administered by continuous intravenous infusion at a dose rate equivalent to administration of reference ala-TFPI at a dose rate of less than about 0.66 mg/kg/hr.

4. The method of claim 3 wherein said dose rate is equivalent to administration of reference ala-TFPI at a dose rate from about 0.00025 to about 0.050 mg/kg/hr and wherein said TFPI or ala-TFPI is administered for at least about 72 hours.

5. The method of claim 4 wherein said dose rate is equivalent to administration of reference ala-TFPI at a dose rate from about 0.010 to about 0.045 mg/kg/hr.

6. The method of claim 5 wherein said ala-TFPI is non-glycosylated.

7. The method of claim 5 wherein said dose rate is equivalent to administration of reference ala-TFPI at a dose rate of about 0.025 mg/kg/hr.

8. The method of claim 7 wherein said ala-TFPI is non-glycosylated.

9. The method of claim 1 wherein said TFPI or said ala-TFPI is administered for at least about 96 hours.

10. The method of claim 9 wherein said ala-TFPI is non-glycosylated.

11. The method of claim 9 wherein said TFPI or ala-TFPI is administered by continuous intravenous infusion to provide a total dose equivalent to administration of reference ala-TFPI at a total dose from about 0.024 to about 4.8 mg/kg.

12. The method of claim 9 wherein said ala-TFPI is non-glycosylated.

13. The method of claim 9 wherein said TFPI or ala-TFPI is administered by continuous intravenous infusion at a dose rate equivalent to administration of reference ala-TFPI at a dose rate of about 0.025 mg/kg/hr.

14. The method of claim 13 wherein said ala-TFPI is non-glycosylated.

15. The method of claim 1 wherein said TFPI or ala-TFPI is administered by continuous intravenous infusion to provide a daily dose equivalent to administration of reference ala-TFPI at a daily dose from about 0.006 mg/kg to about 1.2 mg/kg.

16. The method of claim 15 wherein said ala-TFPI is non-glycosylated.

17. The method of claim 1 wherein said TFPI or ala-TFPI is prepared from a lyophilized composition.

18. The method of claim 17 wherein said ala-TFPI is non-glycosylated.

19. The method of claim 1 wherein said TFPI or ala-TFPI is administered as a formulation comprising arginine.

20. The method of claim 19 wherein said ala-TFPI is non-glycosylated.

21. The method of claim 1 wherein said TFPI or ala-TFPI is administered as a formulation comprising citrate.

22. The method of claim 21 wherein said ala-TFPI is non-glycosylated.

23. The method of claim 1 wherein said TFPI or ala-TFPI has a concentration of about 0.15 mg/ml in a formulation comprising about 300 mM arginine hydrochloride and about 20 mM sodium citrate and having a pH of about 5.5.

24. The method of claim 23 wherein said ala-TFPI is non-glycosylated.

25. The method of claim 1 further comprising administering, at the same time as, or within 24 hours of administering said TFPI or ala-TFPI, an additional agent selected from the group consisting of an antibiotic, an antibody, an endotoxin antagonist, a tissue factor analog having anticoagulant activity, an immunostimulant, a cell adhesion blocker, BPI protein, an IL-1 antagonist, pafase (PAF enzyme inhibitor), a TNF inhibitor, an IL-6 inhibitor, and an inhibitor of complement.

26. The method of claim 25 wherein said ala-TFPI is non-glycosylated.

27. The method of claim 25 wherein said additional agent is an antibody, wherein said antibody binds specifically to an antigen selected from the group consisting of TNF, IL-6, and M-CSF.

28. The method of claim 27 wherein said ala-TFPI is non-glycosylated.

29. The method of claim 1 wherein the demonstrable infection is detected by a positive culture.

30. The method of claim 29 wherein the positive culture is a blood culture.

31. The method of claim 1 wherein the demonstrable infection is detected by a gram stain.

32. The method of claim 1 wherein the patient is not treated with heparin.

33. The method of claim 32 wherein the INR response of the patient to the TFPI or the ala-TFPI is greater than or equal to 1.2 units per 1 µg/ml increase of plasma TFPI or ala-TFPI concentration.

34. The method of claim 32 wherein ala-TFPI is administered and the ala-TFPI is non-glycosylated.

35. The method of claim 32 wherein the demonstrable infection is detected by a chest radiograph.

36. The method of claim 1 wherein the International Normalized Ratio (INR) response of the patient to the TFPI or the ala-TFPI is greater than or equal to 1.2 units per 1 µg/ml increase of plasma TFPI or ala-TFPI concentration.

37. The method of claim 1 wherein the INR response of the patient to the TFPI or the ala-TFPI is less than 1.2 units per 1 µg/ml increase of plasma TFPI or ala-TFPI concentration.

38. The method of claim 1 wherein the patient has community acquired pneumonia.

39. The method of claim 1 wherein the patient has nosocomial pneumonia.

40. The method of claim 1 wherein ala-TFPI is administered and the ala-TFPI is non-glycosylated.

41. The method of claim 1, wherein the ala-TFPI is glycosylated.

42. The method of claim 1 wherein the demonstrable infection is detected by a chest radiograph.

43. A method for treating severe pneumonia, comprising:
administering to a patient having severe pneumonia (i) TFPI or ala-TFPI and (ii) an additional agent selected from the group consisting of an antibiotic, a monoclonal antibody, a cytokine inhibitor, and a complement inhibitor, wherein said patient has a demonstrable infection.

44. The method of claim 43 wherein said ala-TFPI is non-glycosylated.

45. The method of claim 43 wherein said TFPI or ala-TFPI is administered by continuous intravenous infusion at a dose rate equivalent to administration of reference ala-TFPI at a dose rate of less than about 0.66 mg/kg/hr.

46. The method of claim 45 wherein said dose rate is equivalent to administration of reference ala-TFPI at a dose rate from about 0.00025 to about 0.050 mg/kg/hr.

47. The method of claim 43 wherein the demonstrable infection is detected by a chest radiograph.

48. The method of claim 43 wherein the patient is not treated with heparin.

49. The method of claim 48 wherein the demonstrable infection is detected by a chest radiograph.

50. A method of treating severe pneumonia in a patient in need thereof, comprising:
   a) selecting a patient with severe pneumonia, wherein the patient has a demonstrable infection; and
   b) providing said patient with TFPI or ala-TFPI,
   wherein providing TFPI or ala-TFPI to said patient results in treatment of severe pneumonia.

51. The method of claim 50, wherein step (a) comprises selecting a patient with severe community acquired pneumonia.

52. The method of claim 50 wherein the patient is not treated with heparin.

53. The method of claim 50 wherein the demonstrable infection is detected by a chest radiograph.

* * * * *